(12) United States Patent
Roberts, IV et al.

(10) Patent No.: US 8,350,102 B2
(45) Date of Patent: *Jan. 8, 2013

(54) PROCESS FOR CONVERSION OF BIOMASS TO FUEL

(75) Inventors: William L. Roberts, IV, Raleigh, NC (US); H. Henry Lamb, Apex, NC (US); Larry F. Stikeleather, Raleigh, NC (US); Timothy L. Turner, Chapel Hill, NC (US)

(73) Assignee: North Carolina State University, Raleigh, NC (US)

( * ) Notice: Subject to any disclaimer, the term of this patent is extended or adjusted under 35 U.S.C. 154(b) by 170 days.

This patent is subject to a terminal disclaimer.

(21) Appl. No.: 12/897,318

(22) Filed: Oct. 4, 2010

(65) Prior Publication Data

US 2011/0105813 A1    May 5, 2011

Related U.S. Application Data

(63) Continuation of application No. 11/948,006, filed on Nov. 30, 2007, now Pat. No. 7,816,570.

(60) Provisional application No. 60/868,278, filed on Dec. 1, 2006, provisional application No. 60/913,361, filed on Apr. 23, 2007.

(51) Int. Cl.
*C07C 4/00* (2006.01)

(52) U.S. Cl. .......... 585/240; 585/242; 585/733; 44/308; 44/605

(58) Field of Classification Search ................ 585/240, 585/242, 733, 14, 310; 44/308, 605; 208/15, 208/16, 133
See application file for complete search history.

(56) References Cited

U.S. PATENT DOCUMENTS

| 2,139,589 | A |   | 12/1938 | Ittner |
|---|---|---|---|---|
| 2,163,563 | A |   | 6/1939 | Schrauth |
| 4,102,938 | A |   | 7/1978 | Rao |
| 4,300,009 | A |   | 11/1981 | Haag et al. |
| 4,409,092 | A |   | 10/1983 | Johnson et al. |
| 4,992,605 | A | * | 2/1991 | Craig et al. .................. 585/240 |

(Continued)

FOREIGN PATENT DOCUMENTS

CN        1827742 A        9/2006
(Continued)

OTHER PUBLICATIONS

Hermann, Die Pflanzenlecithine [Plant lecithins], Verlag fur chem. Industrie H. Ziolkowsky KG, Augsburg, 1988, p. 181.

(Continued)

*Primary Examiner* — Nina Bhat
(74) *Attorney, Agent, or Firm* — Womble Carlyle Sandridge & Rice, LLP

(57) ABSTRACT

The present disclosure is directed to processes for the direct conversion of lipidic biomass fuelstock to combustible fuels. In particular, the disclosure provides a process for the direct conversion of animal fats to transportations fuels suitable as replacement for petroleum-derived transportation fuels. In an example, the method comprises the steps of hydrolyzing a lipidic biomass to form free fatty acids, catalytically deoxygenating the free fatty acids to form n-alkanes, and reforming at least a portion of the n-alkanes into a mixture of compounds in the correct chain length, conformations, and ratio to be useful transportation fuels. Particularly, the product prepared comprises mixtures of hydrocarbon compounds selected from the group consisting of n-alkanes, isoalkanes, aromatics, cycloalkanes, and combinations thereof.

40 Claims, 11 Drawing Sheets

U.S. PATENT DOCUMENTS

| | | | |
|---|---|---|---|
| 5,233,109 A * | 8/1993 | Chow | 585/241 |
| 5,578,090 A | 11/1996 | Bradin | |
| 5,705,722 A * | 1/1998 | Monnier et al. | 585/240 |
| 6,180,845 B1 | 1/2001 | Catallo et al. | |
| 7,232,935 B2 | 6/2007 | Jakkula | |
| 7,511,181 B2 * | 3/2009 | Petri et al. | 585/240 |
| 7,540,952 B2 * | 6/2009 | Pinho et al. | 208/108 |
| 7,578,927 B2 * | 8/2009 | Marker et al. | 208/67 |
| 7,691,159 B2 * | 4/2010 | Li | 44/605 |
| 7,816,570 B2 * | 10/2010 | Roberts et al. | 585/240 |
| 7,955,401 B2 * | 6/2011 | Ghonasgi et al. | 44/308 |
| 8,067,657 B2 * | 11/2011 | Duarte Santiago et al. | 585/733 |
| 2004/0055209 A1 * | 3/2004 | Jakkula et al. | 44/301 |
| 2004/0074760 A1 | 4/2004 | Portnoff et al. | |
| 2004/0192981 A1 | 9/2004 | Appel et al. | |
| 2004/0230085 A1 | 11/2004 | Jakkula et al. | |
| 2006/0021277 A1 | 2/2006 | Peterson et al. | |
| 2006/0161032 A1 | 7/2006 | Murzin et al. | |
| 2006/0186020 A1 | 8/2006 | Gomes | |
| 2006/0207166 A1 * | 9/2006 | Herskowitz et al. | 44/385 |
| 2006/0236595 A1 | 10/2006 | Nakamura | |
| 2007/0010682 A1 | 1/2007 | Myllyoja et al. | |
| 2007/0135666 A1 | 6/2007 | Koivusalmi et al. | |
| 2007/0135669 A1 * | 6/2007 | Koivusalmi et al. | 585/331 |

FOREIGN PATENT DOCUMENTS

| | | |
|---|---|---|
| EP | 1 741 767 A | 1/2007 |
| EP | 1 741 768 A1 | 1/2007 |
| GB | 594 141 A | 11/1947 |
| WO | WO 2007/027955 A2 | 3/2007 |
| WO | WO2007027955 * | 3/2007 |
| WO | WO 2007/065512 A1 | 6/2007 |
| WO | WO 2007/068795 A | 6/2007 |

OTHER PUBLICATIONS

Kusdiana et al., "Catalytic effect of metal reactor in transesterification of vegetable oil," *J. AOCS 81*:103-104 (2004).

Maier et al. (*Chemische Berichte* 115: 225-229, 1982).

Snåre et al., (*Industrial Engineering Chemistry Research 45*(16): 5708-5715, 2006).

Sonntag, N.O.V., "Fat Splitting", *J. AOCS 56*:A729-A732 (1979).

* cited by examiner

PROCESS FOR CONVERSION OF BIOMASS TO FUEL

CROSS REFERENCE TO RELATED APPLICATION

The present application is a Continuation of U.S. patent application Ser. No. 11/948,006, filed Nov. 30, 2007, which issued as U.S. Pat. No. 7,816,570 on Oct. 19, 2010, which application claims priority to U.S. Provisional Patent Application No. 60/868,278 Filed Dec. 1, 2006, and U.S. Provisional Patent Application No. 60/913,361 Filed Apr. 23, 2007, all of which are incorporated herein by reference in their entirety.

FIELD OF THE INVENTION

The present invention is directed to processes for converting biomass into fuel. More particularly, the processes of the invention allow for conversion of lipidic biomass sources into various hydrocarbons useful as transportation fuels, particularly jet engine fuels, diesel engine fuels, and gasoline engine fuels.

BACKGROUND

Fossil fuels (or petroleum-based fuels) have formed the basis for energy production and transportation in the $20^{th}$ and $21^{st}$ centuries. Increased need among growing populations and emerging nations, as well as market volatilities arising from wars, politics, and natural disasters, have focused worldwide attention on this non-renewable resource. In particular, rising costs and threats of shortages and supply interruptions have recently highlighted the need for alternative fuel sources to petroleum-based products. Biofuels have particularly been a focus for alternative fuels.

Biofuel is generally regarded as being any fuel derived from biomass. The term biomass is often used in regard to plant-based sources, such as corn, soy beans, flaxseed, rapeseed, sugar cane, and palm oil, but the term can generally extend to any recently living organisms, or their metabolic byproducts, that play a part in the carbon cycle.

The production of biofuels to replace fossil fuels is in active development, focusing on the use of cheap organic matter (usually cellulose, agricultural waste, and sewage waste) in the efficient production of liquid and gas biofuels which yield high net energy gain. Biofuels are viewed as environmentally favorable (particularly over fossil fuels) because the carbon in biofuels was recently extracted from atmospheric carbon dioxide by growing plants, and burning the biofuels does not result in a net increase of carbon dioxide in the Earth's atmosphere. Perhaps more importantly, biofuels are a renewable fuel source, and the potentially limitless fuel supply derived therefrom can have a stabilizing effect on fuel prices in the long-term.

One widespread use of biofuels is in home cooking and heating (e.g., wood, charcoal, and dried dung). Biologically produced alcohols, most commonly methanol and ethanol, and to a lesser extent propanol and butanol, can be produced through enzymatic and microbiological fermentation. For example, ethanol produced from sugar cane is widely used as automotive fuel in Brazil, and ethanol produced from corn is being used as a fuel additive in the United States. Gases and oils are also being produced from various waste sources. For example, thermal depolymerization of waste materials (including plants, food, paper, plastic, paint, cotton, synthetic fabrics, sewage sludge, animal parts, and bacteria) allows for extraction of methane and other compounds similar to that obtainable from petroleum.

The need for alternative fuel sources, and particularly biofuels, also extends to high end uses, such as automobile and jet fuels. Almost all high end use fuels (such as jet engine fuel, diesel engine fuel, and gasoline engine fuel) are presently made from petroleum. Accordingly, such fuels are prepared through refining of crude oils. Refining generally encompasses three basic categories of activities: separation, upgrading, and conversion. During separation, feedstock (e.g., crude oil) is separated into two or more components based on some physical property, typically boiling point. The most common separation method is distillation. Upgrading uses chemical reactions to improve product quality by removing unwanted compounds that impart undesirable properties. For example, "sweetening" relates to removal of mercaptans and other organosulfur compounds, which are corrosive. Hydroprocessing uses hydrogen and a catalyst to remove reactive compounds, such as olefins, sulfur compounds, and nitrogen compounds. Clay treating removes polar compounds by passing the fuel stream over a bed of clay particles. Conversion fundamentally changes the molecular structure of the feedstock, usually by cracking large molecules into small molecules (e.g., catalytic cracking and hydrocracking).

FIG. 1 provides a schematic layout of a modern, fully integrated refinery for preparing various fuel types. As seen in FIG. 1, crude oil is fed to the distillation column where straight-run light and heavy gasoline, kerosene, and diesel are separated at atmospheric pressure. The bottoms from the atmospheric column are vacuum distilled to obtain gas oils for fluid catalytic cracking (FCC) or hydrocracker feed. Previously, the vacuum residue might have been used as a low-value, high-sulfur fuel oil for onshore power generation or marine fuel. To remain competitive today, however, refiners must collect as much high-value product as possible from every barrel of crude, and vacuum residue may now be sent to a residue conversion unit, such as a residue cracker, solvent extraction unit, or coker. These units produce additional transportation fuels or gas oils, leaving an irreducible minimum of residue or coke.

The jet fuel produced by a refinery may be all straight-run or hydroprocessed product, or it may be a blend of straight-run, hydroprocessed, and/or hydrocracked product. Small amounts of heavy gasoline components also may be added. Straight-run kerosene from low-sulfur crude oil may meet all of the jet fuel specification properties. Straight-run kerosene, though, is normally upgraded by mercaptan oxidation, clay treating, or hydrotreating before it can be sold as jet fuel. The refinery must blend the available streams to meet all performance, regulatory, economic, and inventory requirements. Sophisticated computer programs have been developed to optimize all aspects of refinery operation, including the final blending step. The refiner really has only limited control over the detailed composition of the final jet fuel product. It is determined primarily by the composition of the crude oil feed, which is usually selected based on considerations of availability and cost. Moreover, the chemical reactions that occur in the conversion process are not specific enough to allow for much tailoring of the products.

The consumption of transportation fuels continues to grow worldwide, particularly in light of the rapidly growing need for transportation in emerging economies. For example, just the consumption of jet fuel in the United States increased from 32 million gallons per day in 1974 to 70 million gallons per day in 1999. Although fuel needs are obviously growing, the number of refineries has not kept up with the growing need. According to the National Petrochemicals and Refiners Association, the last refinery built in the United States was completed in 1976. Between 1999 and 2002, refining capacity in the United States rose only 3 percent. Moreover, public perception and environmental concerns make building new refineries more and more difficult. For example, a report from the California Energy Commission notes that even though 10 refineries representing 20% of the state's refining capacity were closed between 1985 and 1995, it is unlikely that new refineries will be built in California. Accordingly, not only is there a need for increased amounts of transportation fuels, there is also a need for alternative sources (to combat dwindling petroleum supplies and the vicissitudes of the crude oil market) and alternative methods of preparing fuels.

In its Broad Agency Announcement (BAA) 06-43 posted Jul. 5, 2006, the Defense Advanced Research Projects Agency (DARPA) Advanced Technology Office (ATO) began soliciting proposals for biofuels to explore energy alternatives and fuel efficiency efforts to reduce reliance on oil to power its aircraft, ground vehicles, and non-nuclear ships. DARPA's BAA06-43 particularly sought efforts to develop a process that efficiently produces a surrogate for petroleum based military jet fuel (such as the current standard fuel, JP-8) from oil-rich crops produced by either agriculture or aquaculture (including but not limited to plants, algae, fungi, and bacteria) and which ultimately can be an affordable alternative to petroleum-derived JP-8.

Biodiesel has been proposed as an alternative source for jet fuel production; however, current biodiesel alternative fuels are produced by transesterification of triglycerides extracted from agricultural crop oils. Specifically, fats are reacted with alcohols and converted to alkyl esters (biodiesel) followed by conversion of biodiesel to jet fuel. The overall reaction is provided below in Formula (1), $$CH_2(OCOR^1)CH(OCOR^2)CH_2(OCOR^3)+3ROH+ \text{(catalyst)} \rightarrow R^1OCOR+R^2OCOR+R^3OCOR+ CH_2OHCHOHCH_2OH \quad (1)$$

wherein $R^1$, $R^2$, and $R^3$ represent possibly distinct hydrocarbon chains. As seen in Formula (1), one molecule of triglyceride is combined with three alcohol molecules to produce three molecules of biodiesel and one molecule of glycerol. Thus, the transesterification reaction converts the triglyceride triester to three fatty acid alkyl monoesters. This process unacceptably yields a blend of methyl esters (biodiesel) that is 25% lower in energy density than JP-8 and exhibits unacceptable cold-flow features at the lower extreme of the required JP-8 operating regime (−47° C.). For example, kinetic viscosity at 40° C. of fuel prepared in this manner is in the range of 1.9 to 6.0 centistokes, but the viscosity of an acceptable jet fuel should be in the range of about 1.2 centistokes. Further, it is common for such fuels to have a freezing point in the range of about 0° C. Moreover, as feedstock cost is the primary production cost driver in the preparation of jet fuel from biomass, there has heretofore been no process for preparing jet fuel from biomass that is affordable and utilizes a suitably available necessary feedstock material.

There is likewise an increasing need and desire to establish viable alternative fuel sources for other transportation vehicles, particularly automobiles. Alternative fuels, as defined by the Energy Policy Act of 1992 (EPAct), include ethanol, natural gas, propane, hydrogen, biodiesel, electricity, methanol, and p-series fuels. As previously pointed out, biofuels represent a potentially limitless fuel supply that has heretofore been virtually inaccessible. The ability to use biomass as a source for automobile fuels, such as gasoline or diesel, could not only potentially provide lowered gasoline prices due to increased supply but also lessen the demand for crude oil and stem the fear of waning reserves.

Vegetable oils, animal fats, and algae lipids can be converted to a combination of liquid and gaseous hydrocarbons by transesterification, deoxygenation, pyrolysis, and catalytic cracking processes. All of these processes have been developed to varying degrees over the past 100 years. To convert these fuelstocks into fuel, some combination of these processes can be employed, and optimal combination is a function of both the fuelstock and the desired properties of the fuel product. The present invention provides a process for preparing fuel from biomass.

SUMMARY OF THE INVENTION

The present invention provides processes for the preparation of biofuels. In one aspect, the invention provides for the direct conversion of biomass into fuel. In preferred embodiments, the inventive processes provide for direct conversion of lipidic biomass into transportation fuels, such as jet engine fuel, gasoline engine fuel, and diesel engine fuel.

In one embodiment, the inventive process comprises the following steps: (A) performing thermal hydrolysis on a lipidic biomass to form a product stream comprising a free fatty acid and form a by-product stream comprising glycerol; (B) performing catalytic deoxygenation on the free fatty acid stream to form a product stream comprising an n-alkane; and (C) performing one or more reforming steps on the n-alkane stream to form a product stream comprising a mixture of hydrocarbon compounds selected from the group consisting of n-alkanes, isoalkanes, aromatics, and cycloalkanes. Preferably, after step (C), the hydrocarbon compounds are in a combination and ratio necessary to form an overall composition useful as a transportation fuel.

One or more of the individual process steps of the invention can require the application of heat. Process heating can be a particularly costly aspect of many processes. The present invention, however, can make use of reaction by-products for process heating. For example, in one embodiment, the inventive process further comprises recovering at least a portion of the glycerol stream from the hydrolysis step and using the glycerol as a fuel for producing at least a portion of the process heat. Since glycerol is an unavoidable by-product of the hydrolysis of triglyceride-containing lipids, the glycerol forms a particularly cost-effective fuel source. It is only according to the present invention, though, that the use of glycerol as a process heating fuel has been recognized.

In one embodiment of the invention, the thermal hydrolysis step comprises introducing the lipidic biomass into the bottom of a reactor column, introducing water near the top of the reactor column, and heating the reactor. Preferably, the reactor is heated to a temperature of about 220° C. to about 300° C. under a pressure sufficient to prevent the water in the reactor from flashing to steam.

The catalytic deoxygenation step of the inventive process can be carried out in various embodiments. For example, in one embodiment, the catalytic deoxygenation step comprises gas-phase deoxygenation. In another embodiment, the catalytic deoxygenation step comprises liquid-phase catalytic deoxygenation carried out in a hydrocarbon solvent. In both embodiments, the catalyst used is preferably a noble metal, such as palladium. Deoxygenation can also proceed by multiple mechanisms. In one embodiment, deoxygenation comprises decarboxylation. In another embodiment, deoxygenation comprises decarbonylation.

In the liquid phase embodiment, the catalytic deoxygenation is preferably carried out in a hydrocarbon solvent. In such embodiments, the present invention again provides a distinctive benefit. In particular, the present invention realizes the ability to recover a portion of the n-alkane stream formed in the catalytic deoxygenation step. This recovered n-alkane stream can then be used as at least a portion of the hydrocarbon solvent in which the liquid phase catalytic deoxygenation step is carried out. This is beneficial in that is negates the need for introducing a separate solvent, and it also negates the need to add costly heat to bring the solvent up to the reaction temperature and avoid slowing the reaction process.

Deoxygenation according to the present invention can particularly be differentiated from thermal decarboxylation. Specifically, in certain embodiments, catalytic deoxygenation is carried out at a temperature at which deoxygenation does not substantially proceed by thermal action alone. Moreover, catalytic deoxygenation according to the present invention achieves a conversion rate that is not seen in thermal decarboxylation, particularly when carried out at the reaction temperatures used according to the present invention.

The reforming step of the inventive process can comprise a number of separate reactions. For example, in certain embodiments, reforming comprises one or more steps selected from the group consisting of hydroisomerization, hydrocracking, dehydrocyclization, and aromatization. In specific embodiments, reforming comprises the use of a solid catalyst, which preferentially comprises a metal functional component and, optionally, an acidic-functional component. In other embodiments, reforming comprises the use of two or more different catalysts. Moreover, the separate reactions in the reforming step can be carried out in the same reactor or in different reactors. Accordingly, in one embodiment, reforming comprises a first reaction carried out in a first reactor and at least a second reaction carried out in at least a second, separate reactor. Thus, reforming can comprise separating the n-alkane stream into two or more reforming streams and directing the two or more reforming streams separately into the first reactor and the at least second reactor. In still another embodiment, reforming comprises a first reaction carried out in a first reactor, a second reaction carried out in a second, separate reactor, and at least a third reaction carried out in at least a third, separate reactor. Again, the n-alkane stream can be separated into three or more reforming streams that are separately directed into the three or more reactors. In other embodiments, the reactors can be aligned in a series such that a first reforming product stream is formed in the first reactor and proceeds into the second reactor where a second reforming product stream is formed.

The invention is characterized by the ability to use a common feedstock and arrive at specific transportation fuels. In specific embodiments, this arises from the ability to reform the n-alkanes into a variety of compounds representative of the types of compounds which make up common transportation fuels. The correct combination and ratio can be achieved during the reactions of the reforming step such that the reforming product stream is already in the desired combination and ratio of compounds. The invention also encompasses embodiment, however, wherein multiple product streams are recovered from the reforming process, and the streams are combined to form the final product having the desired combination of hydrocarbon compounds in the desired ratio. In specific embodiments, the reforming product stream comprises hydrocarbon compounds in a combination and ratio necessary to form an overall composition useful as a jet engine fuel, a gasoline engine fuel, or a diesel engine fuel. Preferably, the overall composition formed is substantially identical to the counterpart petroleum-derived transportation fuel. Further, it is preferential for the steps of the inventive process to be carried out separately and sequentially.

The present invention is also characterized by the ability to arrive at the desired fuel in an energy efficient manner. Thus, in certain embodiments, the process of the invention exhibits an overall energy efficiency of at least about 75%. Energy efficiency can be calculated as the lower heating value of the produced transportation fuel over the sum of the lower heating value of the process reactants and the total energy input into the process.

The inventive process provides an affordable source of biofuels through conversion of lipidic biomass, such as animal fats, vegetable oils, and algae lipids. In particular, the low cost animal fat fuelstock overcomes the primary production cost driver for biofuels. Biofuels prepared according to the invention are also compliant with specifications generally required for particular types of fuels. For example, jet fuel prepared according to the invention is amenable to on-site fuel characterization and combustion testing to maximize iterative feedback. More particularly, jet fuel prepared according to the invention provides the energy density and cold flow properties required for jet engine fuels, such as JP-8 (i.e., energy density >44 MJ/kg, and cold flow <−47° C.).

Another key benefit of the invention is the unique diversity provided by the lipidic biomass feedstock. In specific embodiments, the lipidic biomass feedstock comprises animal fats, which alone provide a feedstock of approximately 1.5 billion gallons/year in the U.S. However, the feedstock is more diverse, and the invention can use any biomass source comprising triglycerides (both agricultural or aquacultural). The use of lipidic biomass as a fuel feedstock is further beneficial in that it is generally independent from weather-related uncertainties that can plague other biomass fuel sources, such as sugar cane, corn, and the like, which rely on conversion of carbohydrate-based biomass rather than lipid-based biomass. The benefit of lipidic biomass feedstock further lies in the robustness of the fuelstock supply, with the much greater geographic diversity of animal production providing greater security against strategic fuelstock sabotage, relative insensitivity to weather pattern changes, and lower susceptibility to crop failure due to disease or infestations. In other words, geographical variations in lipidic biomass prices can be overcome since the fuel production process can be tailored to accommodate a cheaper biomass source in a given location. Thus, it is clear that the process of the present invention is useful for successfully producing a transportation fuel from a lipidic biomass feedstock wherein the fuel meets all physical and chemical requirements of the particular fuel while also providing an optimal efficiency and scalability.

DESCRIPTION OF THE DRAWINGS

Figure 1:
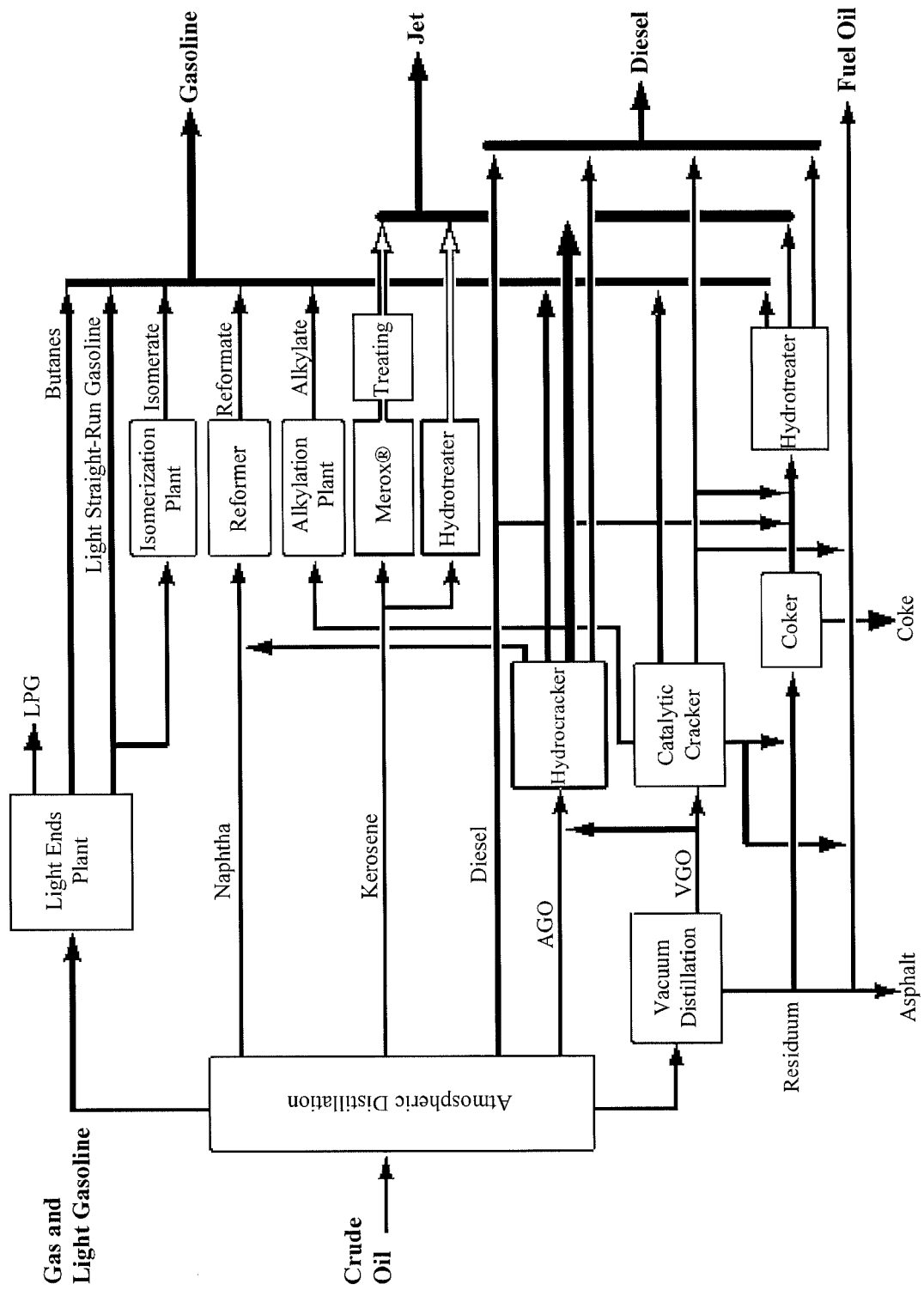
Figure 2:
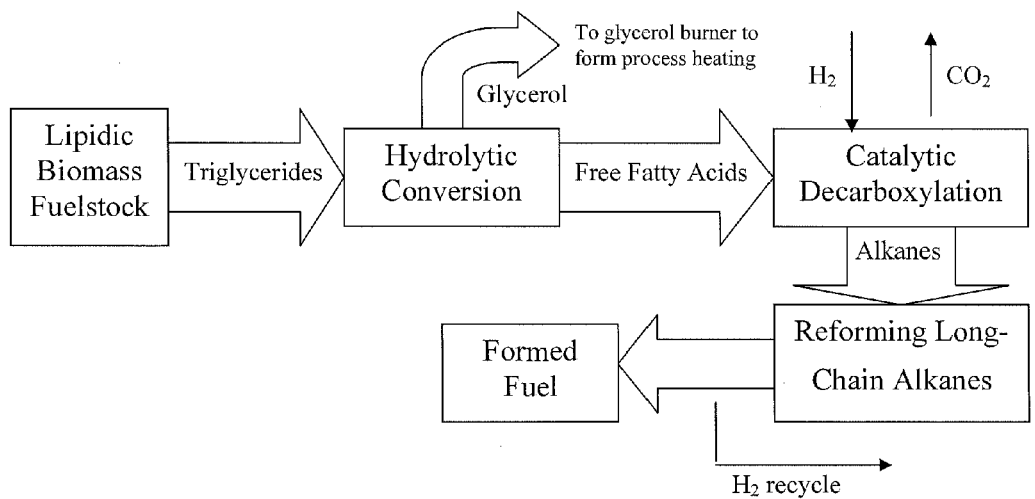
Figure 3:
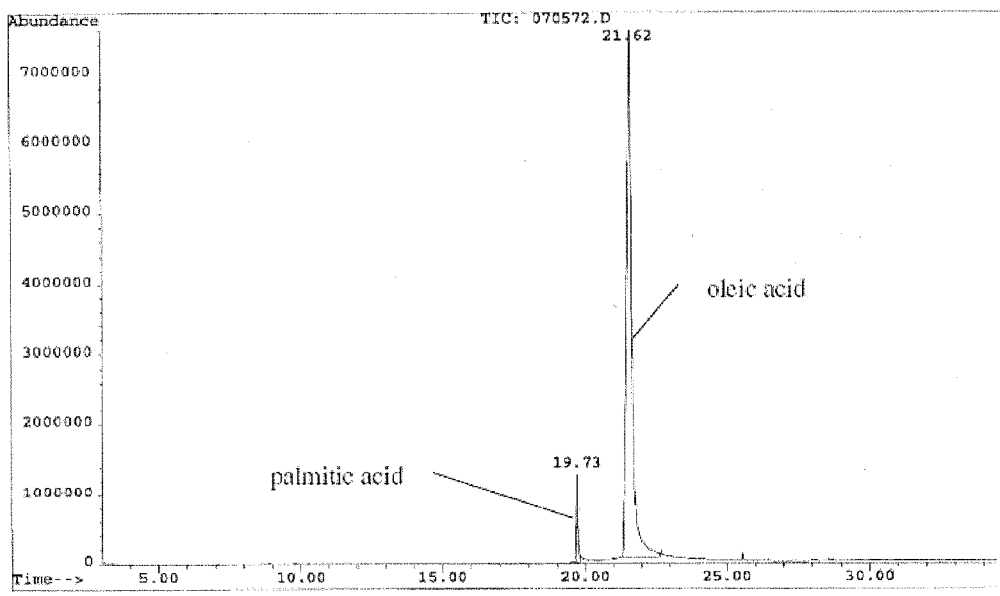
Figure 4:
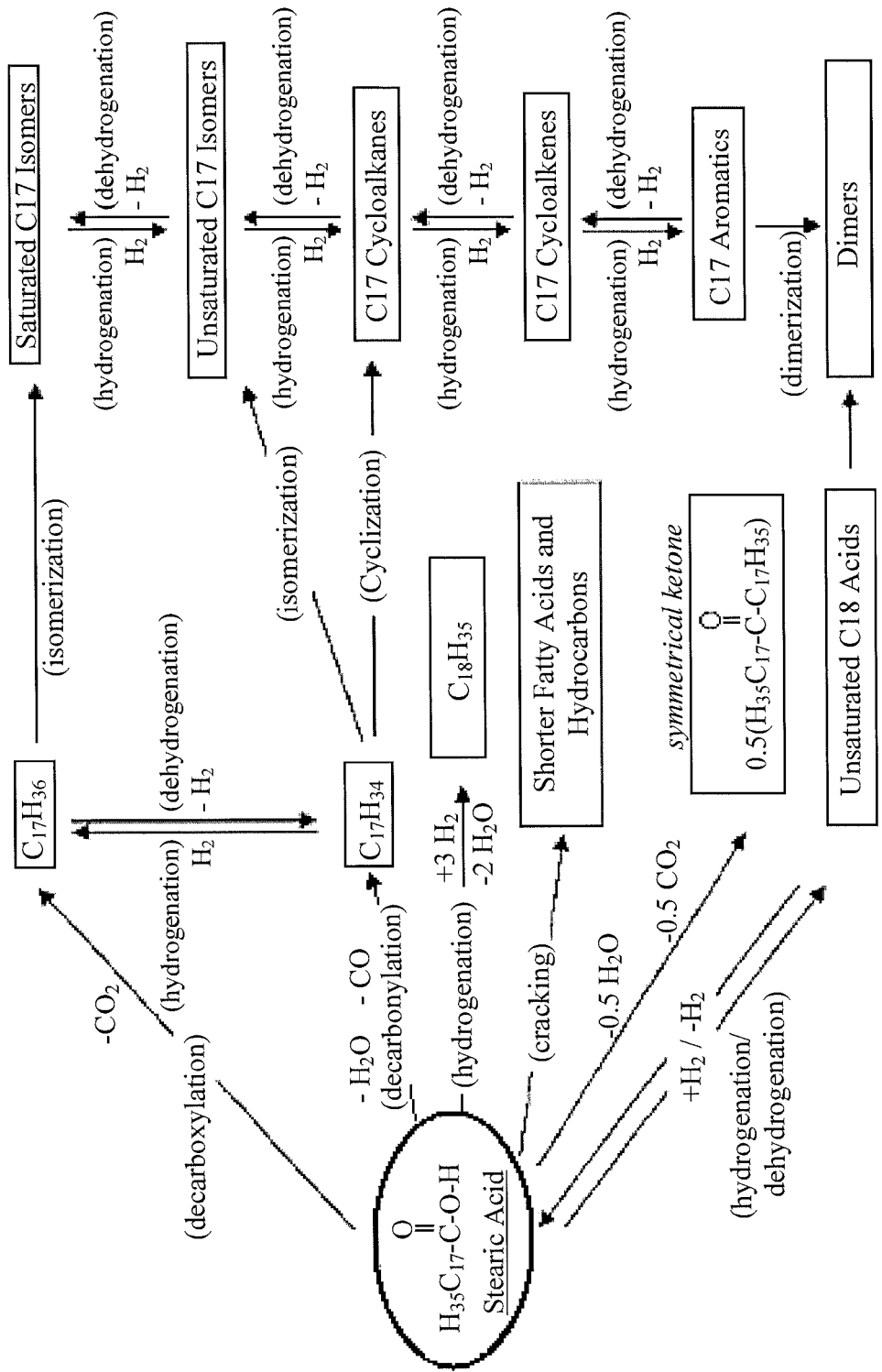
Figure 5:
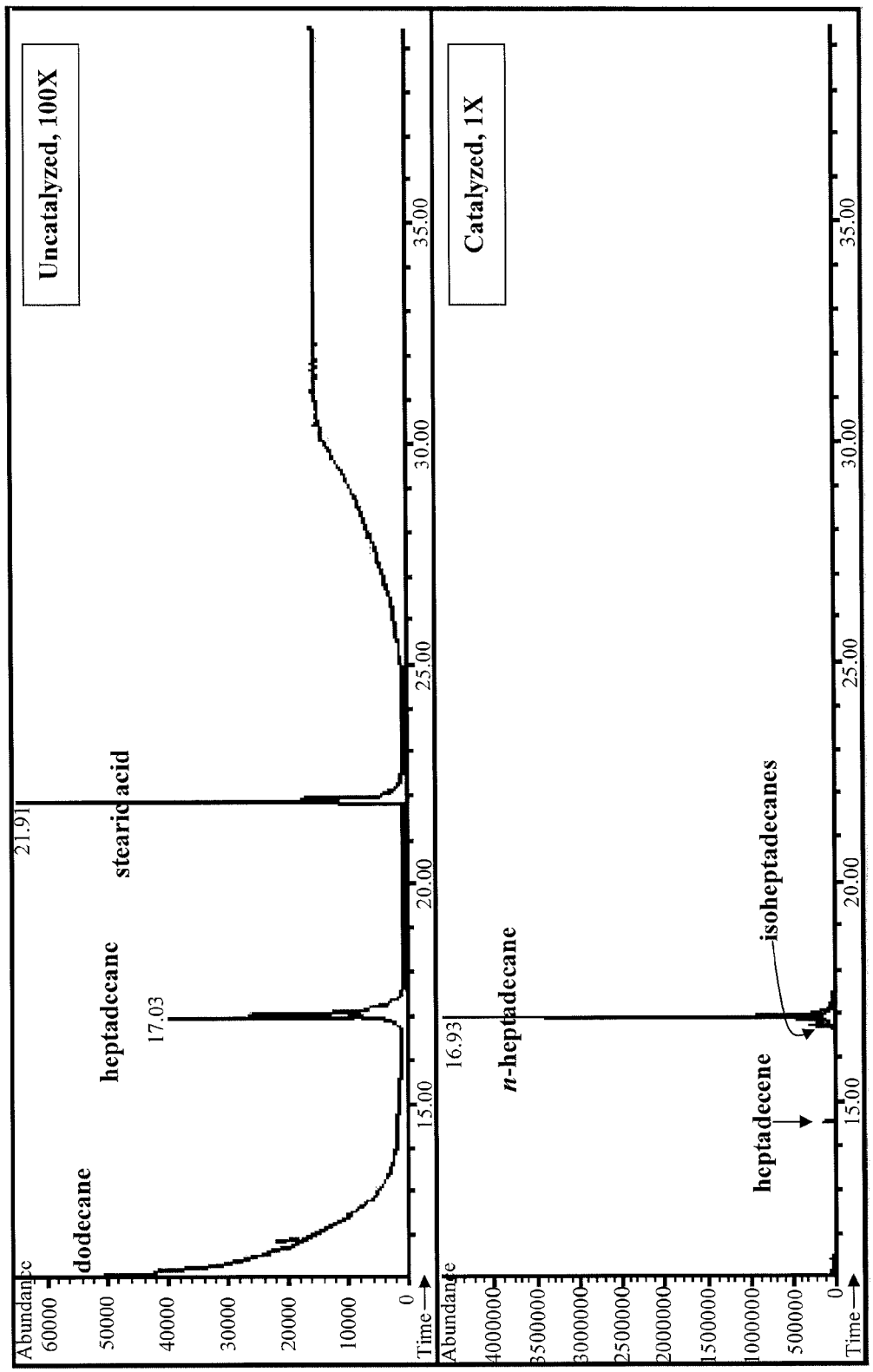
Figure 6:
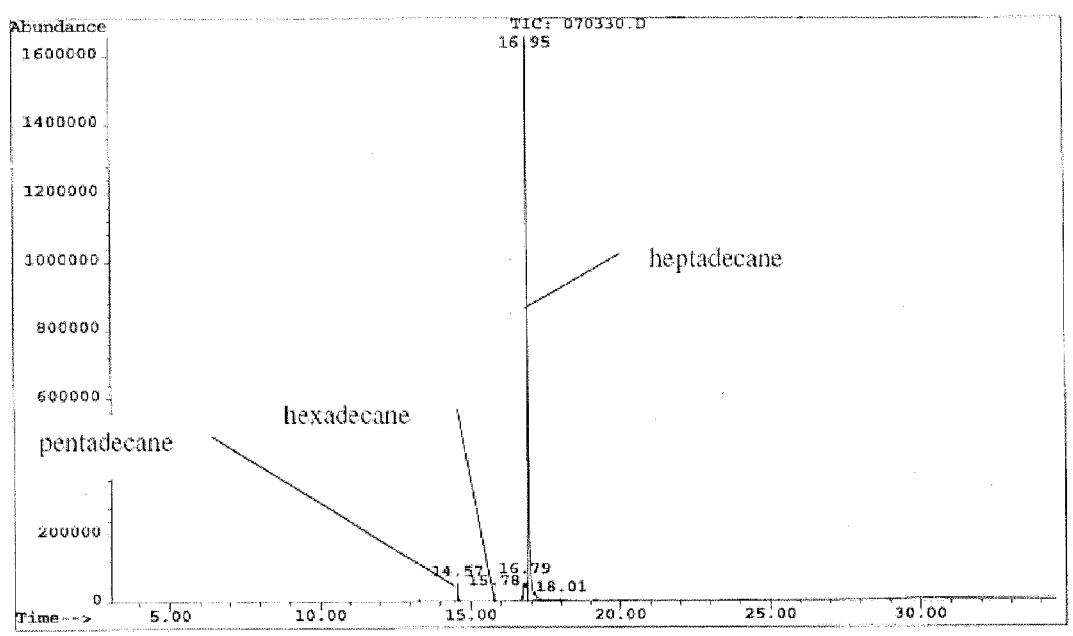
Figure 7:
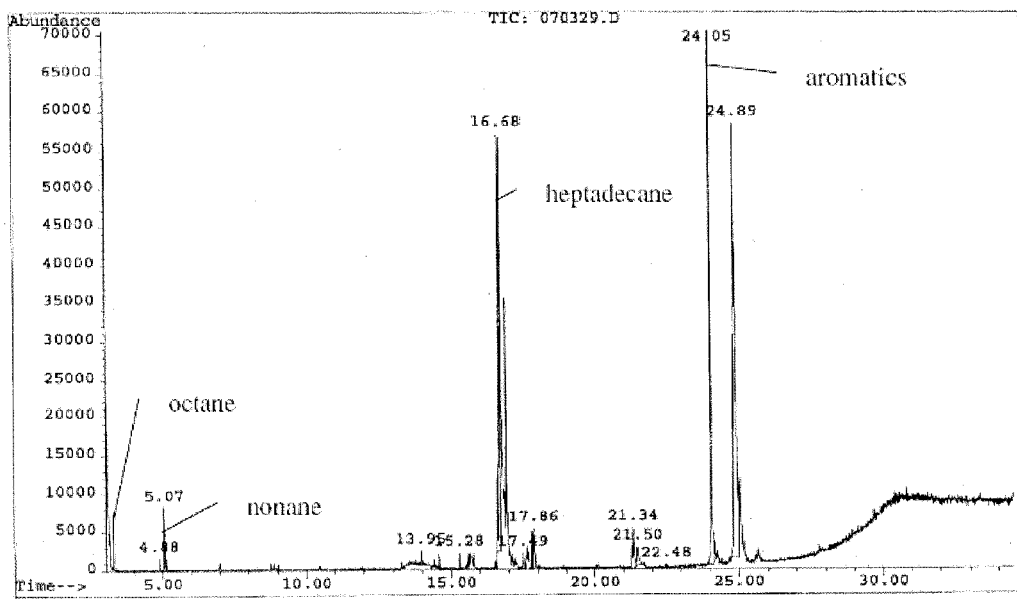
Figure 8:
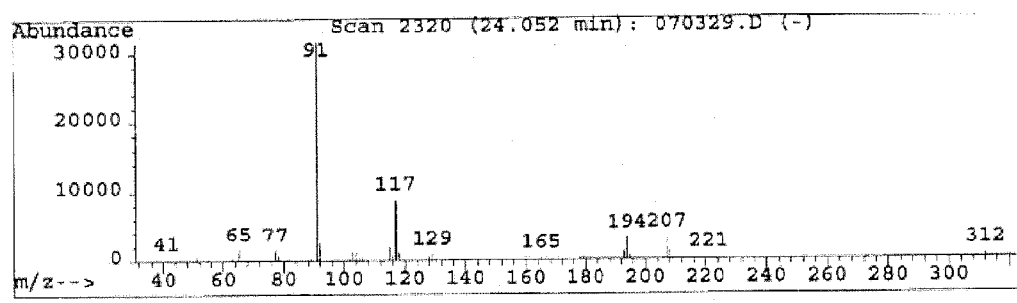
Figure 9:
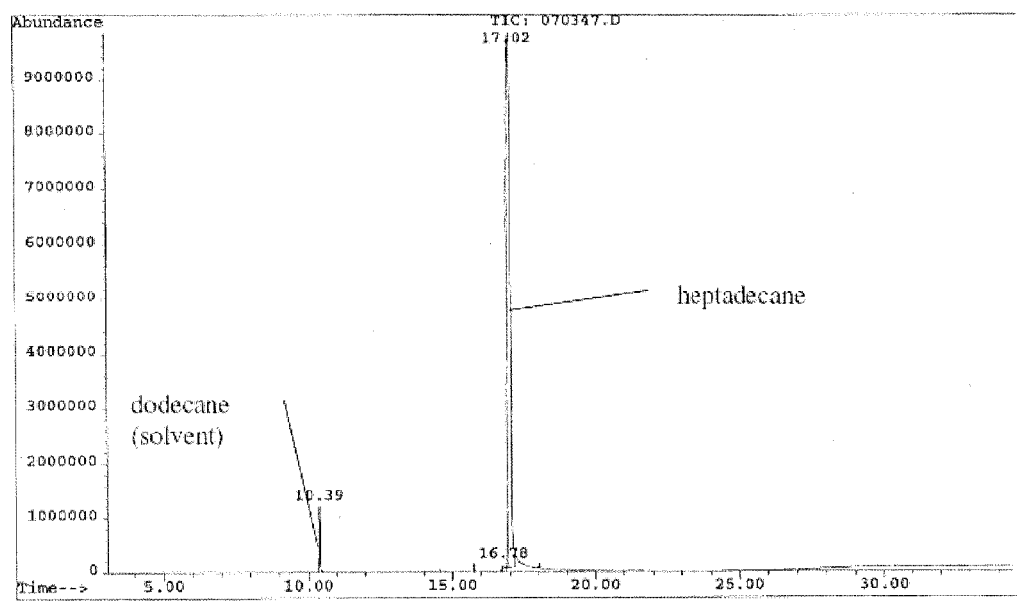
Figure 10:
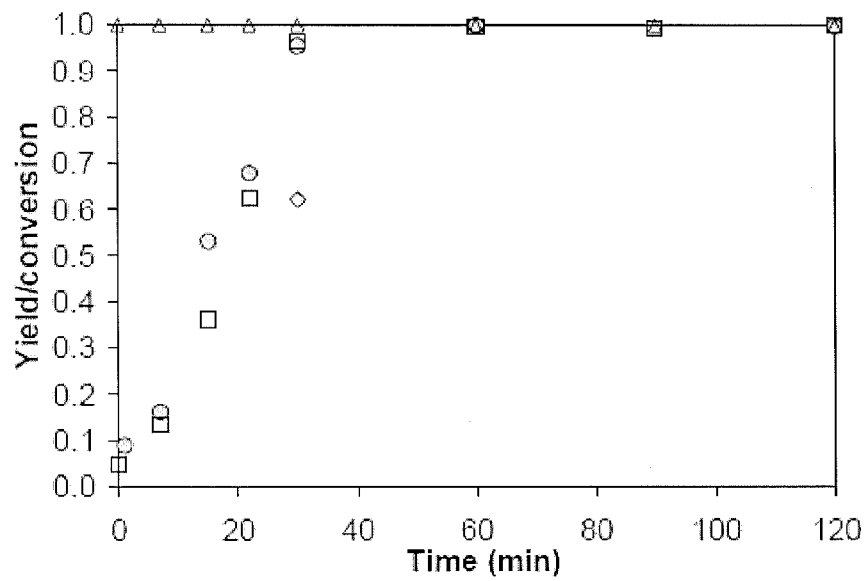
Figure 11:
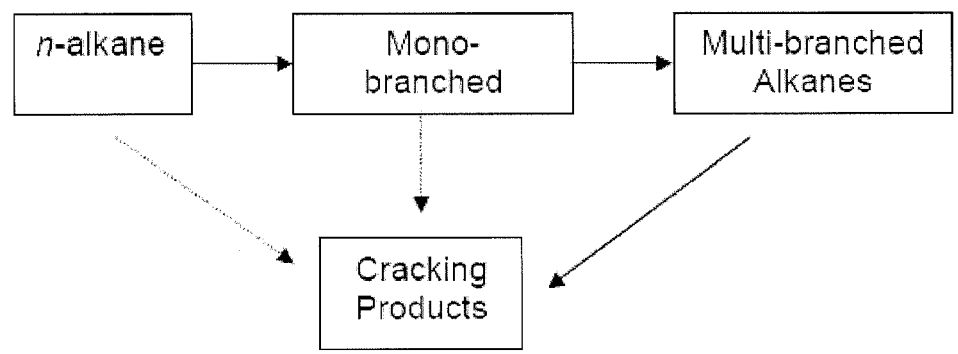
Figure 12:
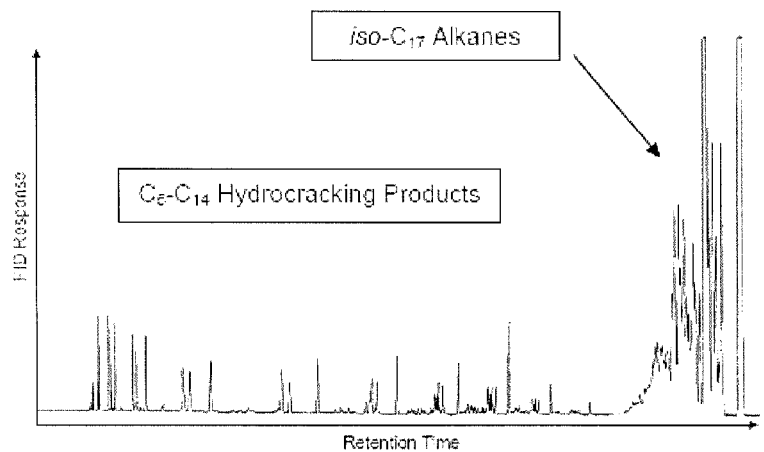
Figure 13:
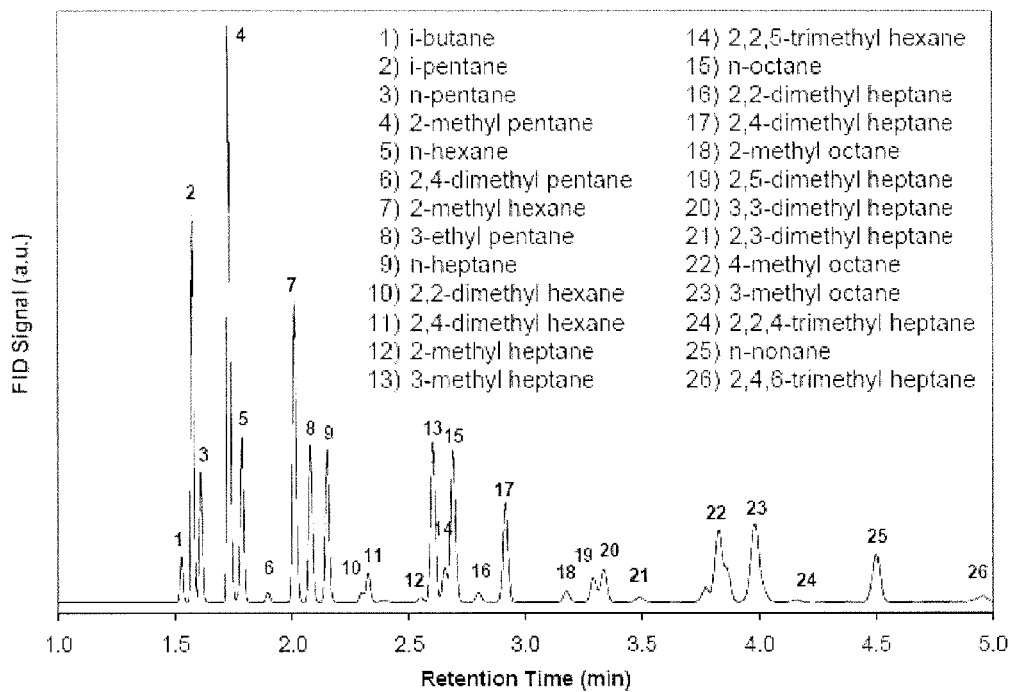
Figure 14:
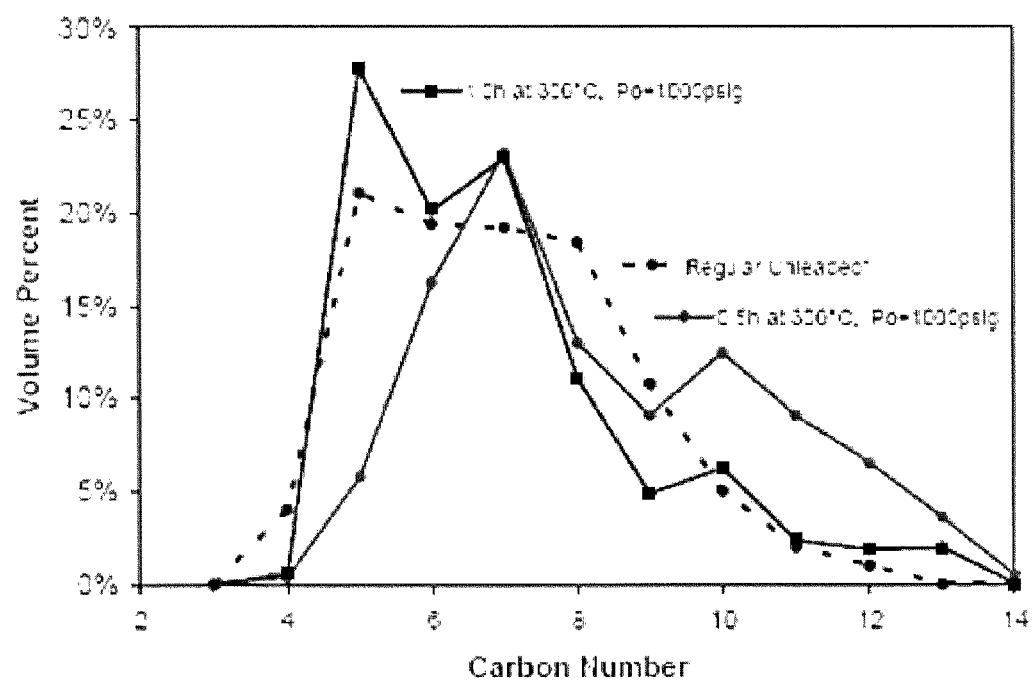
Figure 15:
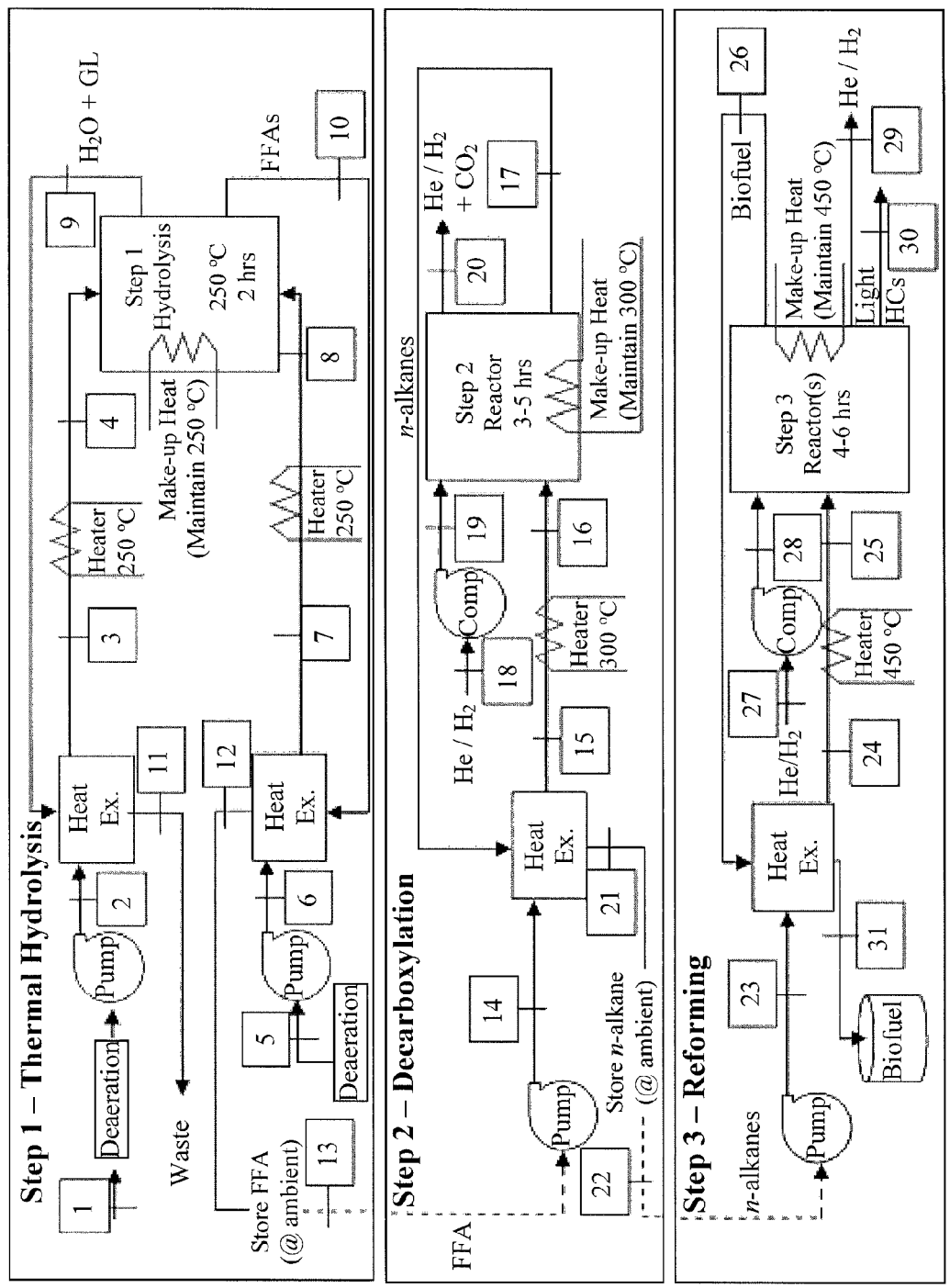

Having thus described the invention in general terms, reference will now be made to the accompanying drawings, which are not necessarily drawn to scale, and wherein:

FIG. 1 is a schematic representation of a typical modern refining process for the preparation of fuels from crude oil;

FIG. 2 is a flowchart illustrating the steps for direct conversion of lipidic biomass to a transportation fuel according to one embodiment of the invention;

FIG. 3 is a graph showing the free fatty acid conversion product of canola oil after undergoing thermal hydrolysis according to one embodiment of the invention;

FIG. 4 is a flowchart illustrating a summary of possible chemical pathways for changing $C_{18}$ fatty acids into fuels;

FIG. 5 is a graph illustrating the difference between uncatalyzed deoxygenation of stearic acid and catalyzed deoxygenation of stearic acid according to one embodiment of the invention;

FIG. 6 is a graph showing the n-alkane conversion product of stearic acid after undergoing catalytic deoxygenation according to one embodiment of the invention;

FIG. 7 is a graph showing the total conversion products of stearic acid after undergoing catalytic deoxygenation according to another embodiment of the invention;

FIG. 8 is a MS graph of the products representing the aromatic peak shown in the graph of FIG. 7;

FIG. 9 is a GC/MS chromatogram of the reaction product of deoxygenation of stearic acid carried out according to one embodiment of the invention;

FIG. 10 is a graph showing the deoxygenation kinetics of stearic acid and oleic acids in $H_2$ according to one embodiment of the invention;

FIG. 11 is a schematic of a typical isomerization/hydrocracking network;

FIG. 12 is a chromatogram showing the reaction products after three hours reaction time in a reforming process according to one embodiment of the invention;

FIG. 13 is a GC-MS chromatogram showing the reaction products of a reforming process according to another embodiment of the invention;

FIG. 14 is a graph showing the carbon number distribution of a gasoline fuel obtained after one hour of batch hydrotreating according to one reforming embodiment of the invention in comparison to the distribution of a typical regular unleaded gasoline; and FIG. 15 is process flow according to one embodiment of the invention showing each process step.

DETAILED DESCRIPTION

The invention now will be described more fully hereinafter through reference to various embodiments, and particularly in regard to the attached figures. These embodiments are provided so that this disclosure will be thorough and complete, and will fully convey the scope of the invention to those skilled in the art. Indeed, the invention may be embodied in many different forms and should not be construed as limited to the embodiments set forth herein; rather, these embodiments are provided so that this disclosure will satisfy applicable legal requirements. As used in the specification, and in the appended claims, the singular forms "a", "an", "the", include plural referents unless the context clearly dictates otherwise.

The present invention provides a process for the preparation of biofuels via direct conversion of biomass feedstock. The term "biofuel" as used herein is understood to mean a composition derived from a non-petroleum biomass and comprised of a mixture of hydrocarbons in the correct chain lengths, chain conformations, and compound ratios to be used as a transportation fuel. A "transportation fuel" as used herein is understood to mean a composition useful as a fuel in internal combustion engines, such as commonly found in transportation vehicles (e.g., automobiles, airplanes, trains, and heavy machinery), the composition including, but not limited to, a composition classifiable as a jet engine fuel, a diesel engine fuel, or a gasoline engine fuel.

The inventive process is characterized by feedstock flexibility, high process efficiency, effective utilization of process by-products, and the ability to deliver a biofuel that is substantially identical to a petroleum-derived fuel product. In other words, the biofuel is formed of classes of compounds in the same ratios necessary to effectively function in the same manner as the petroleum-derived furl. In the process of the present invention, triglycerides can be converted to free fatty acids (FFAs) by hydrolysis and the glycerol byproduct and unreacted water can be separated, so that the first step in the multi-step process yields only FFAs for use in further process steps. The FFAs can then be decarboxylated/deoxygenated in a catalytic process to produce the n-alkane corresponding to the FFA alkyl tail group. Finally, the resulting mixture of alkanes (and alkenes) can be hydroisomerized/hydrocracked to produce a mixture of isoalkanes (i.e., branched alkanes) and n-alkanes. The mixture can further be isomerized/aromatized to form aromatics, such as toluene and naphthalenes, or cyclized to form cycloalkanes.

The present invention particularly allows for the direct conversion of oils with high free fatty acid content into a blend of hydrocarbon compounds useful as fuels, including jet fuel, diesel, and gasoline. Oils from feedstocks, such as agricultural crops (e.g., soybean oil, canola oil, and palm oil), aquacultural crops (e.g., algae), energy crops, animal fats, and waste grease, can be converted to a combination of liquid and gaseous hydrocarbons by various chemical mechanisms including transesterification, deoxygenation, pyrolysis, and catalytic cracking, which processes have been developed to varying degrees. However, to prepare a useful fuel, such as gasoline, diesel, or jet fuel, it is not possible to simply pick and choose from among known chemical processes. In other words, the mere existence of such processes does not lead to an overall process for preparing a useful fuel. Rather, it is necessary to employ an exact combination of processes in an exact order under specific conditions, and the present process is inventive in part because of the ability to recognize the exact combination of process steps and the exact reaction parameters useful to take a common lipidic biomass feedstock and convert it into the desired fuel product, whether it be gasoline, diesel, jet fuel, or another combustible fuel formed of a specific combination of hydrocarbons.

Since there is a tremendous investment in the current transportation fuels infrastructure, for any fuel to gain mass market penetration, it must be compatible with the existing infrastructure. The biofuels produced according to the process of the present invention are virtually identical chemically and physically to their counterpart petroleum-derived fuels, thus making their introduction into the fuels market seamless. This is highly advantageous over current fuel alternatives (e.g., the gasoline alternative ethanol), which require engine modification for substantial use, and which can also require special handling. For example, ethanol must be transported to distribution points by special carrier because of ethanol's hygroscopic nature and tendency to absorb water. Providing fuel from a renewable biomass according to the present invention does not require establishment of a new distribution network, such as would be necessary with fuel alternatives, such as ethanol, hydrogen, and the like. Rather, fuel prepared according to the invention can be directly introduced into the existing distribution network and commingled with petroleum-derived fuel.

Biofuels prepared according to the present invention also can be customized to provide desirable qualities, particularly taking into account the above factors that must be considered in preparing a specific fuel type. For example, jet fuel (Jet-A, Jet A-1, and JP-8) is a middle distillate fraction that contains a mixture of straight and branched chain alkanes, aromatics, and cycloalkanes. Carbon chain lengths of 10 to 14 are typical. Petroleum-derived jet fuels contain approximately 20% aromatics by volume, and these species contribute directly to the production of particular matter in the exhaust and an ideal jet fuel would have lower aromatic content. However, due to the elastomer seals in the jet engines, aromatics in the fuel are necessary to prevent the seals from shrinking, thereby causing fuel leaks. Further, high energy density (by weight) and good cold-flow properties are critical for jet fuels.

Diesel fuel is composed primarily of $C_{10}$-$C_{20}$ hydrocarbons. A diesel fuel is characterized principally by its Cetane Index, which is a measure of the fuel's propensity to auto-ignite on compression. Normal hexadecane (cetane) is assigned a Cetane Index of 100, and branched alkanes and aromatic compounds have lower Cetane Indices. To improve cold flow properties, as required for an all-weather diesel fuel, a trade-off is made in Cetane Index by introducing some branched alkanes. A typical Cetane Index for petroleum diesel is around 50.

Gasoline is comprised mainly of $C_5$-$C_{12}$ alkanes, isoalkanes, and aromatics. Gasoline is characterized by Octane Number, which is a measure of the fuel's propensity to resist auto-ignition on compression (and hence fuels with high Octane Numbers have low Cetane Indices). Branched alkanes and aromatics have higher Octane Numbers than normal (linear) alkanes. For example, iso-octane (2,2,4-trimethylpentane) has an Octane Number of 100, whereas n-octane has an Octane Number of 0.

In a specific embodiment, a jet fuel can be prepared to match the chemical kinetics of Jet-A/JP-8 fuel comprising a dominant isoalkane composition and that provides an energy density of >44 kJ/kg, produces less soot than petroleum-derived JP-8, and has equivalent or improved low-temperature viscosity in relation to JP-8. One example of a chemical kinetic surrogate for JP-8 is shown Table 1. A jet fuel matching the physical properties of JP-8 would be expected to have a similar composition (i.e., similar ratios of n-alkanes, isoalkanes, cyclics, and aromatics).

TABLE 1

| Compound | Wt. % |
|---|---|
| n-dodecane | 43% |
| iso-cetane | 27% |
| methylcyclohexane | 15% |
| 1-methylnaphthalene | 15% |

Further, Table 2 summarizes the ability of the process of the present invention, in one embodiment, to provide a JP-8 fuel that meets or exceeds the performance required according to U.S. military specifications.

TABLE 2

| JP-8 Fuel Property | U.S. Military Specification | Jet Fuel Prepared by Inventive Process |
|---|---|---|
| Energy density (gravimetric) | >42.8 MJ/kg | 44.0 MJ/kg |
| Flash point | >38° C. | 42° C. |
| Freezing point | <−47° C. | −48° C. |
| Low-temp viscosity (−20° C.) | <8.0 centistokes | 4.5 centistokes |
| Aromatic content | <25.0 vol. % | app. 8% |
| Hydrogen content | >13.4 wt. % | 14.7% |
| Density at 15° C. | 0.775-0.840 kg/L | app. 0.8 kg/L |
| Smoke point | >25.0 mm | >25.0 mm |
| Sulfur, total mass % | <0.3% | app. 0% |

In further embodiments, the biofuels prepared according to the invention also include a desirable content of aromatics and cycloalkanes to meet all jet fuel properties (such as energy density, combustion quality, low-temperature fluidity, reduced volatility, and kinetic properties, e.g., carbon:hydrogen ratio and flame speed). Chemical kinetic properties of the fuel are very important, and the process of the invention particularly allows for in-house jet engine testing that can lead to optimal distribution of jet fuel components, such as n-alkanes, isoalkanes, cycloalkanes, and naphthenes.

The process of the invention comprises three consecutive steps: (1) thermal hydrolysis of triglycerides (such as present in a lipidic biomass feedstock) to produce free fatty acids; (2) catalytic deoxygenation (e.g., decarboxylation) of the FFAs from step (1) to form n-alkanes; and (3) reforming of the n-alkanes from step (2) to produce the desired product distribution. These process steps are summarized by the flowchart provided in FIG. 2.

In step (1), hydrolytic conversion of triglycerides (TG) to free fatty acids, a triglyceride-containing biomass feedstock is heated in the presence of water to sever the bonds in the triglyceride molecule between the fatty acid chains and the glycerol backbone. This step generally results in a product mixture of FFAs and glycerol (GL). The overall reaction for this process step is shown in Formula (2).

TG+3H$_2$O→3FFA+GL 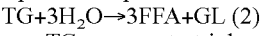 (2)

where TG represents triglyceride and FFA represents free fatty acids. The initial hydrolysis reaction allows for accommodation of a broad array of lipidic feedstocks.

In step (2), catalytic deoxygenation of free fatty acids to their corresponding alkanes, the FFAs are specifically reacted in the presence of a catalyst. As described below in more detail, deoxygenation can proceed by decarboxylation or decarbonylation (although decarboxylation is typically the main reaction pathway. The overall reaction for a decarboxylation process is provided in Formula (3).

$$FFA \rightarrow n\text{-alkane} + CO_2 \qquad (3)$$

This process step can occur in a hydrocarbon solvent, and the present invention is particularly characterized in that the n-alkanes prepared can be recycled as the solvent to maximize thermodynamic efficiency. Gas-phase deoxygenation (i.e., solvent-free) can also be used. The catalytic deoxygenation reaction parameters can be designed to provide the additional benefit of partial dehydrogenation. This can be particularly useful to form a desired amount of unsaturated hydrocarbons (e.g., alkenes).

In step (3), the n-alkanes undergo reforming, such as by hydroisomerization/hydrocracking (HI/HC) and aromatization, to produce a biofuel comprising the desired mixture of isoalkanes, n-alkanes, aromatics, and cycloalkanes. Reforming can be accomplished in a continuous flow stirred reactor, preferentially using a catalyst. The overall reaction for this step is provided in Formula (4).

$$n\text{-alkanes} \rightarrow \text{isoalkanes} + n\text{-alkanes} \qquad (4)$$

The reforming step can be adjusted as needed to produce the proper mixture of isoalkanes, n-alkanes, aromatics, and cycloalkanes to achieve the necessary physical, chemical, kinetic, and material interaction properties useful in the desired fuel product. In certain embodiments, the reforming steps are adjusted to produce a mixture of hydrocarbons wherein the majority are isoalkanes (e.g., greater than about 50% by weight, greater than about 60% by weight, greater than about 70% by weight, or greater than about 75% by weight, based on the overall weight of the hydrocarbon mixture).

The present invention particularly arises from the identification of the specific steps useful to sequentially transform a lipid into a combination of hydrocarbon compounds in the correct chain lengths, correct chain conformations, and correct ratios to provide a useful biofuel, such as biogasoline, biodiesel, or bio-jet fuel. Others have attempted to transform oils into fuels, but such previous attempts do not achieve the controlled efficiency and reproducibility of the present invention. For example, by separately performing deoxygenation and reforming according to the present invention it is possible to optimize the different catalysts used in the individual steps and thereby provide the necessary increased yield of isoalkanes in the $C_7$-$C_{14}$ range to form specific fuel types. Moreover, by performing the catalytic deoxygenation is a separate step, it is possible to provide an oxygenate-free hydrocarbon stream that can be reformed to produce a broad range of bio-based transportation fuels, including gasoline, diesel, and jet fuel.

The present invention is further beneficial in that by adjusting the reaction conditions (such as by increasing reaction temperatures and lowering hydrogen pressures), the process can be optimized to favor the formation of ring structures. For example, in certain embodiments, the process parameters can be controlled such that the biofuel produced from the conversion of the biomass feedstock includes the correct proportions of aromatics and naphthenes to match the kinetic parameters of petroleum JP-8. Such an optimized process step is shown in Formula (5).

$$n\text{-alkanes} \rightarrow \text{isoalkanes} + \text{aromatics} + \text{naphthenes} \quad (5)$$

In other embodiments, the process parameters can be controlled such that the biofuel produced includes the correct proportions of isoalkanes and aromatics, particularly $C_8$ isoalkanes, to match the kinetic parameters of standard gasoline. Such an optimized process step is shown below in Formula (6).

$$C_{15\text{-}17}\text{alkanes} \rightarrow C_8\text{isoalkanes} + \text{aromatics} \quad (6)$$

The inventive process is further characterized in that it can be optimized to utilize reaction by-products. For example, as noted above, the n-alkanes prepared according to Formula (3) above can be recycled as the hydrocarbon solvent in liquid phase embodiments of the deoxygenation step. Furthermore, the glycerol prepared according to Formula (2) above can be used as a thermal source for the above reactions. Combustion of glycerol can be according to Formula (7) below.

$$C_3H_5(OH)_3 + 3.5O_2 \rightarrow 3CO_2 + 4H_2O \quad (7)$$

Biomass Feedstock

The process according to the present invention utilizes biomass as a starting material and directly converts the biomass to a combustible fuel. The term "biomass", as used herein, means living and recently living biological material, or their metabolic byproducts, that play a part in the carbon cycle. Biomass as used in the present invention is preferably derived from renewable sources and, as such, typically excludes commonly recognized fossil fuels (such as crude oil, natural gas, and coal). While such fossil fuels are preferably not used as biomass in the present invention, in certain embodiments, the biomass used in the inventive process can include a minor percentage of compounds directly recognized as fossil fuels, or derivatives thereof.

Preferentially, the biomass used as a fuelstock in the present invention comprises lipidic biomass. The term "lipid" generally refers to compounds that are relatively insoluble in water and generally soluble in nonpolar organic solvents. As used herein, lipids include fats, waxes, oils, and related and derived compounds. More specifically, lipids include monoglycerides, diglycerides, triglycerides, terpenes, phospholipids, fatty alcohols, sterols, fatty acids, and fatty acid esters. Thus, "lipidic biomass" according to the invention includes any biomass having a content of lipidic material. Preferably, lipidic biomass comprises material wherein a majority of the content, or the entire content, of the material comprises lipids.

In preferred embodiments, the lipidic biomass used in the invention is selected from the group consisting of vegetable oils, animal fats, and algae lipids. Generally, any material, though, subject to formation of free fatty acids via hydrolytic reactions can be used in the inventive process. Moreover, any material providing a source of triglycerides can be used in the invention.

Soybean oil has received much attention as an abundant oil bearing crop, although more than 350 oil bearing crops have been identified to date, and any such vegetable oil, seed oil, or nut oil could be used in the invention. In addition to these existing oil crops, other lipidic biomass sources useful in the invention include algae and other aquaculture crops, as well as strategic crops (such as cuphea), bacterial crops, and animal fats. This broad range of useful feed materials is beneficial because it allows for the use of the cheapest and most readily available feedstock at any given time or location. Accordingly, the process of the invention can be utilized in a variety of locations and is not limited to a ready availability of a specific feedstock.

Particularly advantageous for use according to the invention are animal fats, which generally contain a combination of saturated and unsaturated carboxylic acids, especially $C_{16}$ and $C_{18}$ carboxylic acids, and such animal fats have a number of advantages over vegetable oils. In particular, animal fats are generally cheaper than vegetable oils. Examples of animal fats that can be used in the invention include beef fat (tallow), hog fat (lard), turkey fat, and chicken fat, as well as any other vegetable oil or lipid. Lipidic biomass sources providing a majority of $C_{16}$ and $C_{18}$ carboxylic acids are particularly useful in the preparation of jet fuels, as the inventive process is particularly useful for converting such starting materials to the $C_{10}$-$C_{14}$ compounds typically present in jet fuels and other kerosene-type fuels. Similarly, biomass sources providing a majority of $C_{15}$-$C_{17}$ carboxylic acids are particularly useful in the preparation of gasoline since the inventive process, in specific embodiments, is particularly useful for converting such starting materials to a majority of compounds in the $C_8$ range, such as typically present in gasoline. Furthermore, the inventive process can advantageously make use of waste vegetable oils as fuelstock.

The use of lipidic biomass as a fuelstock in the present invention also allows for a diversity of sources, which limits shortages and decreases regional effects, such as weather. Moreover, the process can actually function to recycle waste materials. The process is not limited to the use of virgin materials. Rather, the lipidic biomass can comprise recycled fats, oils, and other lipids as well. For example, cooking fats and greases used in restaurants and fast-food chains can be a source of fuelstock in the present invention. Still further, the present invention provides an alternative to disposal of animal fats from large-scale meat production facilities. Tyson Foods, for example, reported in 2006 that it produces 2.3 billion pounds of animal fat per year. Moreover, vegetable oils are available in an amount of approximately 5 billion gallons per year. Thus, the lipidic biomass used as a fuelstock in the present invention can take on a diversity of forms and sources that can provide a constant supply biofuel through the direct conversion process of the invention.

The fatty acid composition of fats and oils depends on the source. Since these are natural products, there is a range of typical compositions encountered, as shown below in Table 3, which provides the fatty acid content of some common fats and oils.

TABLE 3

| Fat/Oil | Saturated wt. % | | | | | Mono-unsaturated wt. % | | | | Poly-unsaturated wt. % | |
|---|---|---|---|---|---|---|---|---|---|---|---|
| | $C_{12}$ | $C_{14}$ | $C_{16}$ | $C_{18}$ | $>C_{18}$ | $<C_{16}$ | $C_{16}$ | $C_{18}$ | $>C_{18}$ | $C_{18}(2)^a$ | $C_{18}(3)^b$ |
| Soybean |  | 0.3 | 7-11 | 2-5 | 1-3 |  | 0-1 | 22-34 |  | 50-60 | 2-10 |
| Corn |  | 0-2 | 8-10 | 1-4 |  |  | 1-2 | 30-50 | 0-2 | 34-56 |  |
| Tallow | 0.2 | 2-3 | 25-30 | 21-26 | 0.4-1 | 0.5 | 2-3 | 39-42 | 0.3 | 2 |  |
| Lard |  | 1 | 25-30 | 12-16 |  | 0.2 | 2-5 | 41-51 | 2-3 | 3-8 |  |

[a] Linoleic acid;
[b] Linolenic acid

The present invention is particularly beneficial in that it accommodates the use of any of the types of feedstocks represented in Table 3, regardless of the differing fatty acid contents.

In certain embodiments, it is useful for the lipidic biomass to undergo one or more process steps prior to entry into the fuel production process described below. Such additional process steps can be directly included into the process of the invention (i.e., could be inserted into a continuous process described herein immediately upstream of the hydrolysis step). In other embodiments, additional processing of the biomass can take place separately from the process of the present invention.

In one embodiment, it is useful to degum the lipidic biomass, particularly when the lipidic biomass comprises a vegetable oil, such as soybean oil. The mucilage substances in plant oils consist primarily of mixtures of phosphatides, with the amount and composition being dependent on the type of oil seed and the method of obtaining the oil. The great majority of phosphatides can be separated from their micellar solutions by means of hydratization, and used for obtaining lecithin. This process is referred to as wet degumming. A small portion of phosphatides is not hydratizable and remains in the oil. The chemical nature of these "non-hydratizable phosphatides" (NHP) is not completely clear, however, studies have shown that they consist of calcium and magnesium salts of phosphatide acids, in a proportion of more than 50% (see Hermann Pardun, Die Pflanzenlecithine [Plant lecithins], Verlag fur chem. Industrie H. Ziolkowsky K G, Augsburg, 1988, page 181). The goal of conventional technical degumming processes is to remove the non-hydratizable phosphatides from the oil to the greatest extent possible.

Examples of degumming processes include the "Superdegumming process" and the "Unidegumming" process of the Unilever company, the "Total Degumming ("TOP") process" of the Vandemoortele Company, the "Alcon process" of the Lurgi company, and the "UF process" of the company Krupp Maschinentechnik GmbH. In many instances, traditional aqueous degumming for removing hydratizable phosphatides is integrated into these processes, or precedes them. Degumming can particularly comprise a single stage acid treatment (e.g., using phosphoric or citric acid) and a single stage hot water treatment followed by continuous removal of the hydrated gums in a degumming super centrifuge. See, for example, U.S. Pat. No. 4,698,185, which is incorporated herein by reference. Degumming can also proceed by enzymatic processes, such as described in U.S. Pat. No. 6,001,640, which is incorporated herein by reference.

Hydrolysis of Lipidic Biomass

The lipidic biomass used in the process of the invention is first subjected to a hydrolytic conversion process to form free fatty acids. The lipidic biomass used in the invention, and particularly animal fats, can vary over a wide range in purity and quality. Further, many fat sources contain water and are mixtures of fatty acids, fatty alcohols, and fatty-acid esters. The process of the invention takes into account the diversity in the lipidic biomass fuelstocks and handles this variation in fat composition and quality by using a first stage fat splitting process to produce high quality fatty acids which then constitute the main feed for downstream stages. This first stage fat splitting process has the added benefit of simultaneously producing a fuel source to drive the overall process of the invention. As further described below, the glycerol produced in the hydrolysis step can be recovered and used as a combustible heat source. The flowchart of FIG. 2 illustrates the removal of glycerol from this step and transfer into a glycerol burner, which provides the heat needed to at least partially drive the reactions of the invention.

Processes of fat splitting have been described in the art and are well established in the fatty acid industry. See Sonntag, N.O.V., "Fat Splitting", J. AOCS 56:A729-A732 (1979), which is incorporated herein in its entirety. Examples of fat splitting processes include the following: a) the Twitchell process developed in 1898, which involves atmospheric boiling of fat in the presence of various reagents; b) medium pressure autoclave splitting with a catalyst, such as ZnO; c) low pressure splitting in the presence of a catalyst using superheated steam to interact with oil in a tube type reactor; d) continuous, high pressure uncatalyzed countercurrent splitting; and e) enzymatic fat splitting. More recently, studies have demonstrated fat splitting by water hydrolysis using temperatures in the range of 250° C. and water in the subcritical state at pressures of 5 to 20 MPa and reaction times of approximately 20 minutes. See Kusdiana, D., and Saka, S. "Catalytic effect of metal reactor in transesterification of vegetable oil," J. AOCS 81:103-104 (2004), which is incorporated herein by reference. This subcritical process can be carried out in either batch mode or in a continuous reactor, but large amounts of excess water are typically required to drive the reversible hydrolysis reaction to completion. For oils, such as rapeseed oil, the water-to-oil molar ratio can be up to approximately 217:1 (a volume ratio of approximately 4:1). The aqueous phase and the fatty acids come off in liquid form and can be separated.

In a particular embodiment, the continuous, high-pressure, uncatalyzed countercurrent splitting process is used employing a reaction tower or column. This fat splitting process is particularly characterized by high temperatures and high pressures and continuous removal of liberated glycerol with a water stream. This process is particularly efficient and inexpensive for large scale production of saturated fatty acids from fats and oils.

Countercurrent splitting is particularly advantageous in that it is possible to approach complete reaction without the use of excessive amounts of water. To achieve this result, it is beneficial to maintain a residence time in the reactor of about 1 hour to about 4 hours, about 1.5 hours to about 3.5 hours, about 1.5 hours to about 3 hours, about 1.5 to about 2.5 hours, or about 2 hours at the reaction temperature. In light of the residence time, it is possible to use reaction temperatures on the lower end of the preferred temperature scale. For example, in certain embodiments, countercurrent splitting can be carried out at a temperature of about 240° C. to about 260° C., about 245° C. to about 255° C., or about 250° C.

In other embodiments, it is possible to carry out the hydrolysis in a quasi-batch mode. Such embodiments are beneficial in that residence time in the reactor can be greatly reduced. Preferably, such embodiments are carried out at reaction temperatures on the higher end of the preferred temperature scale. For example, in certain embodiments, the quasi-batch hydrolysis can be carried out at a temperature of about 270° C. to about 290° C., about 275° C. to about 285° C., or about 280° C. Under such conditions, reaction time can be reduced to less than about 1 hour, less than about 45 minutes, or less than about 30 minutes. Preferably the reaction time is about 5 minutes to about 30 minutes, about 10 minutes to about 20 minutes, or about 10 minutes to about 15 minutes.

When using the quasi-batch process, it is useful to use a water-to-oil volume ratio that is somewhat greater than required in the countercurrent process. In the quasi-batch process, it is useful for the ratio to be about 3:1 to 1.5:1, about 2.5:1 to about 2:1, or about 2.3:1 v/v (water:oil). In the countercurrent process, however, the water-to-oil ratio is preferably less than about 1.5:1, more preferably less than about 1.25:1, even more preferably less than or equal to about 1:1 v/v (water:oil).

It is also possible, according to the invention, to combine the above methods to provide an optimized process. For example, the reaction can be carried out in a continuous, countercurrent process at a temperature more typically used in the quasi-batch process (e.g., about 280° C.). In such an embodiment, it possible to provide continuous processing with a residence time on the order of about 10 minutes to about 20 minutes, preferably about 10 minutes to about 30 minutes.

In one embodiment, the fat is introduced by a sparge ring from the bottom of the reactor column with a high pressure feed pump. Water is introduced near the top of the column, and the mass flow rate of the water is preferably in the range of about 25% to about 75% of the mass flow rate of the fat being introduced at the bottom of the column. More preferably, the water flow rate is about 30% to about 60% or about 40% to about 50% of the mass flow rate of the fat. Actual mass flow rates can be determined by the volume of the reactor such that residence time of the fat is on the order of 2 to 3 hours.

When hydrolysis proceeds in a continuous process (e.g., countercurrent flow), it is beneficial for the reactor to include a sensor for detecting the interface level between the oil and the water/glycerin volumes. For example, the sensor can be an electrical impedance probe positioned at the interface and useful for sensing a change in impedance if the interface level moves so that the probe is in water rather than oil/fat (and vice versa). If the interface level rises so that the probe is in the water, impedance will tend to drop to a much lower value, and this provides a control signal that the system needs to allow more of the water/glycerin mixture to exit the reactor while holding FFAs. This can be achieved, in certain embodiments, by having two pressure relief valves: one for FFAs and one for the water/glycerin mixture. These pressure relief valves can be provided in series with on/off valves controlled by the interface signal sensor in such a way as to maintain the desired interface level in the reactor during continuous influx (pumping) of the oil/fat and water reactants. This allows for maintaining direct control of the mass flow ratios without requiring precise, direct control of mass flow rates over long time periods.

The fat rises through the hot glycerol-water collecting section at the bottom of the column and passes through the oil-water interface into the continuous phase, the oil layer in which hydrolysis takes place. Direct injection of high-pressure steam quickly heats the reaction mixture to the desired temperature. In certain embodiments, hydrolysis is carried out at a temperature of about 220° C. to about 300° C. In further embodiments, hydrolysis is carried out at a temperature of about 230° C. to about 290° C., about 240° C. to about 280° C., or about 250° C. to about 270° C. In one embodiment, the temperature is raised to about 260° C.

Heating of the hydrolysis reactor can be by any useful method. In certain embodiments, heating can be via electromagnetic induction of the reactor vessel. In such embodiments, preheated water can be injected near the reaction temperature into the vessel. In a specific embodiment, it is possible to preheat the water to a saturation pressure slightly above the hydrolysis vessel operating pressure, which can induce steam production upon entry into the reaction vessel. In specific embodiments, the supply of reaction products entering the reaction vessel is also heated to avoid artificially lowering the process temperature of the hydrolysis reactor. For example, the supply lines for the reactants (particularly sections of the lines that are immediately prior to entry into the hydrolysis reactor) can be coiled around the exterior of the hydrolysis reactor but within the reactor insulation blanket.

Preferably, the pressure of the reactor column is great enough to keep the water in the reactor from flashing to steam. Thus, at any given temperature during the hydrolysis is carried out, the minimum pressure tracks the P-T line for water between the triple point and the critical point. At any given temperature, the pressure can be greater than this minimum so long as the pressure does not exceed reactor limitations. Therefore, the reactor pressure during hydrolysis is preferably maintained at a pressure greater than the steam pressure so as to maintain the water in a liquid phase. For example, when the reactor temperature is about 260° C., the pressure required to maintain the water in a liquid state is approximately 700 PSIA (4.8 MPa). Thus, in certain embodiments, the reactor pressure during hydrolysis is maintained in the range of about 0.5 Mpa to about 20 MPa, about 1 MPa to about 15 MPa, about 2 MPa to about 10 MPa, or about 4 MPa to about 8 MPa.

The process of the invention splits fats in 98-99% efficiency with little or no discoloration of the fatty acids and an efficient use of steam. Fatty acids coming from the top of the reaction tower can be injected directly into stage two after pressure/temperature adjustments to match the requirements of the deoxygenation process. A mixture of water and glycerol can be removed from the bottom of the reactor. While other processes the may produce glycerol as a by-product simply remove it as an unwanted impurity, the process of the present invention utilizes the produced glycerol as an important reaction product that serves to greatly improve the overall efficiency of the process. The importance of the produced glycerol is further described below.

In preferred embodiments, fats and water supplies are degassed/de-aerated before injection into the splitting tower. Oxygen removal is particularly desirable to prevent unwanted side-reactions during the inventive process. De-aeration can be carried out according to any appropriate method. For example, de-aeration can be achieved by application of a vacuum for a period of time sufficient to remove oxygen from the reactants. De-aeration can further include circulating the liquid to be de-aerated so as to expose all layers of the liquid and enable entrapped gasses to overcome the surface tension and escape the liquid. In specific embodiments, such as when the lipidic biomass comprises highly saturated materials, such as beef tallow, de-aeration is preferably performed after pre-heating the material to maintain a liquid state. De-aeration is preferably carried out upstream from the hydrolysis injection pumps.

The ability to convert lipidic biomass to free fatty acids through an initial hydrolysis step is illustrated in FIG. 3. In one embodiment, virgin canola oil was converted to FFAs by heating the oil in the presence of water to a temperature of about 260° C. at a pressure of about 5 MPa. The FFA conversion rate was 100%, with the significant conversion products being oleic acid ($C_{18}$) and palmitic acid ($C_{16}$).

Catalytic Deoxygenation of FFAs

Following the conversion of the lipidic biomass to free fatty acids, the FFAs are converted to straight-chain paraffins (i.e., n-alkanes) via a reduction process. This step can be carried out in the gas phase (e.g., using a fixed bed catalyst) or in the liquid phase (e.g., using a stirred autoclave reactor with a catalyst slurry/dispersion).

Although reduction processes have been previously performed, the present invention recognizes that catalytic reduction processes are needed to provide reliable, consistent deoxygenation of the FFAs produced in step one of the inventive process to provide a constant stream of n-alkanes for the final step of the inventive process. Accordingly, the reduction process according to the invention generally comprises contacting FFAs with an appropriate catalyst. In one embodiment, the FFAs can be passed through a fixed-bed catalyst, such as palladium on carbon (Pd/C). In another embodiment, the FFAs can be combined with a slurry of Pd/C in a stirred autoclave using solvent.

Deoxygenation is generally understood as relating to a chemical reaction resulting in the removal of oxygen. In the present invention, deoxygenation of FFAs is a reversible reaction that can proceed in either of two mechanisms, which are shown below in Formula (8), wherein R is a hydrocarbon chain.

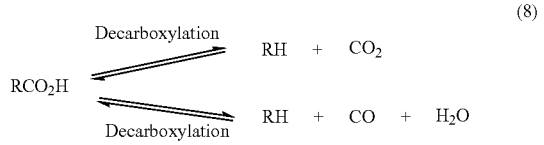

(8)

While decarboxylation and decarbonylation will both proceed over a Pd/C catalyst, decarboxylation is the primary reaction pathway, and the rate of decarboxylation is generally at least an order of magnitude faster than that of decarbonylation. When the n-alkane reaction product from the deoxygenation reaction is used as the reaction solvent (which is more fully described below) and the deoxygenation reaction is performed under hydrogen, the decarbonylation pathway is more significant, since it is not slowed due to microscopic reversibility. It is notable, however, that stearic acid decarboxylation is much slower in heptadecane solvent with a 10% $H_2$ atm. The reaction is driven toward the reaction product by constant 10% $H_2$ sparge, which purges the formed $CO_2$ from the reactor. This is illustrated in Formula (9) and is also more fully described below. The decarboxylation rate is slowed in heptadecane due to equilibrium limitations as seen in this scheme. The decarbonylation pathway is unaffected by the change in solvent since both CO and heptadecane are kept at low concentrations keeping the reverse decarbonylation reactions to a minimum.

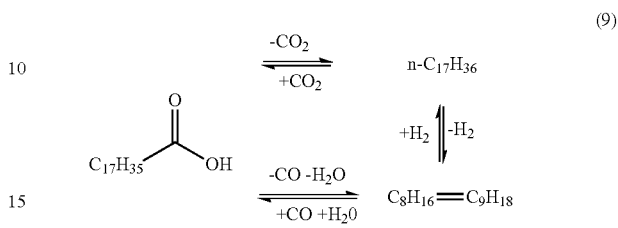

(9)

According to the present invention, this "step 2" reaction pathway can generically be referred to as a reduction reaction or a deoxygenation reaction. Both terms are meant to encompass both the decarboxylation reaction and the decarbonylation reaction. Since decarboxylation is the primary reaction pathway, particularly when using preferred catalysts, the discussion relating to conversion of FFAs to n-alkanes may be particularly described in terms of the decarboxylation reaction. However, the invention is not to be considered as being limited to decarboxylation. Rather, a decarbonylation mechanism is fully encompassed by the invention, particularly in embodiments where n-alkane product is recycled as the reaction solvent.

Although decarboxylation can be achieved through application of high heat in the presence of a high boiling solvent, such thermal decarboxylation is ineffective for complete and consistent reaction of FFAs into their corresponding n-alkanes. In comparison, however, catalytic decarboxylation according to the present invention provides for very good selectivity and a conversion rate approaching 100%. In specific embodiments, the catalytic decarboxylation has a conversion rate to the corresponding n-alkane of at least about 70%, at least about 75%, at least about 80%, at least about 85%, at least about 90%, at least about 92%, at least about 95%, at least about 96%, at least about 97%, at least about 98%, or at least about 99%.

The ability to achieve complete conversion is particularly illustrated in FIG. 5, which shows the results of one evaluation of catalyzed versus uncatalyzed decarboxylation. Specifically, stearic acid was decarboxylated into heptadecane in a 50 mL continuously stirred autoclave reactor using dodecane as a solvent under either catalytic or non-catalytic conditions. In both tests, the stearic acid was heated to 300° C. at 1.5 MPa pressure for varying residence times. In the first test, no catalyst was used. In the second test, a 5% Pd/C catalyst was used.

As shown in FIG. 5, the upper graph shows a small rate of conversion of stearic acid to heptadecane with a large residual amount of stearic acid remaining. In particular, the graph of the uncatalyzed decarboxylation is show at 100× magnification so that the conversion graph is visually meaningful (i.e., showing an abundance of heptadecane of approximately 40,000). In contrast, the lower graph shows a nearly 100% conversion of stearic acid to heptadecane. Note that the graph of catalyzed decarboxylation is shown at 1× magnification, and the abundance of heptadecane in the catalyzed reaction is in excess of 4,000,000 (i.e., more than 100 times greater conversion than in the uncatalyzed reaction). Thus, FIG. 5 clearly illustrates the superior results obtained using catalytic decarboxylation as opposed to thermal decarboxylation alone.

Decarboxylation of carboxylic acids was first reported by Maier, et al. (*Chemische Berichte* 115: 225-229, 1982) using gas-solid (heterogeneous) catalysis over supported palladium and nickel catalysts in the presence of hydrogen. For straight-chain carboxylic acids, palladium was preferred over nickel. The longest straight-chain acid investigated by Maier et al. was octanoic acid ($C_8$). According to the present invention, however, it is possible to successfully decarboxylate a longer chain carboxylic acid (e.g., $C_{18}$ compounds, such as stearic acid, or even higher carbon compounds) in the gas phase. Such gas phase decarboxylation generally comprises vaporization of the lipidic feedstock. For example, in one embodiment when using a feedstock comprising stearic acid, it is necessary to heat to a temperature of at least about 361° C. (the boiling point of stearic acid).

Gas phase catalytic deoxygenation can be carried out by injecting the FFAs from the hydrolysis step into a suitable reactor vessel in fluid communication with a catalyst chamber and heating to a temperature suitable to vaporize the FFAs. The vaporized FFAs move through the catalyst chamber where conversion to the corresponding n-alkane on the order of 100% is achieved. The product can then proceed through a cooling zone for condensation of the n-alkanes. In certain embodiments, it can be useful to purge the system with $H_2$ to remove oxygen prior to heating to the FFA vaporization temperature.

The results of gas phase decarboxylation of stearic acid according to one embodiment of the present invention are illustrated in FIG. 6 through FIG. 8. Specifically, stearic acid was heated to a temperature of at least 361° C. in the presence of a 5% Pd/C catalyst to achieve gas phase decarboxylation. As shown in FIG. 6, the desired product, n-heptadecane, was formed as the major reaction product. The small amounts of hexadecane and pentadecane formed are believed to arise from impurities present in the starting material, which further illustrates the ability to effectively form n-alkanes in the decarboxylation step of the invention.

In another embodiment, stearic acid was again heated to a temperature of at least 361° C. in the presence of a 5% Pd/C catalyst to achieve gas phase decarboxylation. As shown in FIG. 7, the desired product, n-heptadecane, was again formed. Gas phase decarboxylation in this case was also shown to effect cracking, cyclization, and aromatization. The highest peak in FIG. 7 (shown at time 24.05) belongs to a group of benzene derivatives, and the corresponding mass-spectrometer (MS) plot of this peak is provided in FIG. 8. The small peak at 77 indicates the benzene ion, the molecular weight of benzene being about 78 da. The ability to effect these further reactions can be particularly beneficial depending upon the type of fuel desired for production. For example, since jet fuel typically contains roughly 20% aromatic components, such reaction could be useful to forming a product stream that is specifically designed for jet fuel production. This could reduce the amount of further reactions needed in the reforming step of the present invention to arrive at the desired fuel product. In addition to stearic acid, gas phase decarboxylation according to the present invention has been shown to be effective in other $C_{18}$ acids, such as oleic acid and linoleic acid.

Liquid phase deoxygenation is also effective according to the present invention. For example, FIG. 9 is a GC/MS chromatogram of the reaction product of decarboxylation of stearic acid carried out using a 50 mL stirred autoclave reactor. The stearic acid in a dodecane solvent was heated to about 300° C. while contacted with a 5% Pd/C catalyst. As seen in FIG. 9, heptadecane is formed as the major reaction product. As also seen in FIG. 9, the dodecane solvent is also present in the reaction product. Thus, when such a typical solvent is used, it is necessary to isolate the reaction product from the solvent prior to introducing the reaction product into step three of the inventive process.

Snåre, et al. (*Industrial Engineering Chemistry Research* 45(16): 5708-5715, 2006) investigated the deoxygenation of stearic acid as an alternative process for biodiesel production from FFAs using a liquid-phase batch process with dodecane as the solvent (requiring a solvent-to-FFA mass ratio of 19:1). As pointed out above, a separation process was required to recover the products and remove the solvent. According to the present invention, however, it is possible to carry out liquid phase decarboxylation of stearic acid in heptadecane, which is the decarboxylation product of stearic acid. Thus, in certain embodiments, the present invention provides for liquid phase catalytic decarboxylation of a long chain FFA into its corresponding n-alkane while recycling a portion of the reaction product as the solvent. Employing the product of the reaction as the solvent greatly increases the thermodynamic efficiency because the need to heat a separate solvent stream is eliminated. This is further advantageous because it eliminates the need for an additional separation process because the product and the solvent are the same. Thus, the continuous nature of the inventive process is conserved by recycling a portion of the decarboxylation reaction stream as the decarboxylation solvent in a liquid phase reaction.

As previously noted, deoxygenation is a reversible process, and there can thus be equilibrium limitations on the decarboxylation and/or decarbonylation reactions taking place. For example, when using recycled n-alkane reaction product as reaction solvent, deoxygenation can be slowed in both the decarboxylation and decarbonylation pathways. Accordingly, in certain embodiments, it is beneficial to including a purging step to facilitate reaction. For example, removal of $CO_2$ (a decarboxylation product) can be useful to drive equilibrium toward reactants, as illustrated in Formula (8).

Since decarboxylation is the dominant deoxygenation pathway over a Pd/C catalyst, hydrogen generally is not required for the reaction. Nevertheless, in specific embodiments, it can be particularly useful to introduce hydrogen into the reaction. Table 4 below provides the results of one evaluation of the liquid phase decarboxylation of saturated and unsaturated $C_{18}$ FFAs using a Pd/C catalyst in the presence and absence of $H_2$. As seen in Table 4, the decarboxylation of unsaturated FFAs, such as oleic acid, only proceeds to a significant extent in the presence of $H_2$. In this evaluation, decarboxylation was carried out at a temperature of 300° C. and a pressure of 15 atm using 1.6 g of each reactant and 350 mg of Pd/C catalyst. The first five tests were carried out using 23 g of dodecane solvent. The final test with stearic acid was carried out using 23.6 g of heptadecane as solvent. Thus, the present invention is further beneficial in that the decarboxylation reaction parameters can be optimized, such as inclusion or exclusion of $H_2$, depending upon the feedstock composition and the desired end product. Moreover, the beneficial aspect of using recycled decarboxylation product as the decarboxylation solvent (Test 6 in Table 4) does not adversely affect the conversion of the FFA to its corresponding n-alkane. Moreover, the present invention is further beneficial, as illustrated in FIG. 2, in that at least a portion of the $H_2$ used in this decarboxylation step can be provided as a recycled waste stream from the reforming step described in detail below.

TABLE 4

| Test Number | FFA Reactant | Reaction Atmosphere | Reactant Conversion (%) | Heptadecane Yield (wt. %) | Other $C_{17}$ Yield (wt. %) |
|---|---|---|---|---|---|
| 1 | Stearic | He | 92 | 76 | 16 |
| 2 | Stearic | 10% $H_2$ | 100 | 100 | 0 |
| 3 | Oleic | He | 12 | 1 | 7 |
| 4 | Oleic | 10% $H_2$ | 100 | 100 | 0 |
| 5 | Linoleic | 10% $H_2$ | 100 | 100 | 0 |
| 6 | Stearic | 10% $H_2$ | 100 | 100 | 0 |

The deoxygenation kinetics of stearic acid and oleic acids in $H_2$ are closely similar, as shown in FIG. 10, with complete FFA conversion occurring in approximately 30 minutes and providing essentially 100% yield of n-heptadecane. Specifically shown in FIG. 10 is the results of stearic and oleic acid decarboxylation reactions in 10% $H_2$ and dodecane solvent at 300° C. over 5% Pd/C catalyst for different reaction times. Shown are oleic acid conversion (Δ), oleic acid heptadecane yield (□), stearic acid heptadecane yield (○), and oleic acid result with ½ catalyst (◇).

The results shown in FIG. 10 indicate that oleic acid is hydrogenated first to stearic acid before decarboxylation to n-heptadecane. This is shown below in Formula (10).

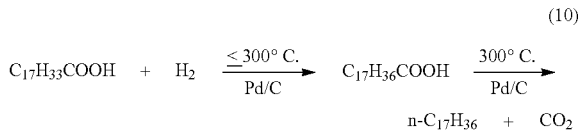

$$C_{17}H_{33}COOH + H_2 \xrightarrow[Pd/C]{\leq 300° C.} C_{17}H_{36}COOH \xrightarrow[Pd/C]{300° C.} n\text{-}C_{17}H_{36} + CO_2 \quad (10)$$

Other known processes that purport to form fuels rely heavily on the use of $H_2$ as a reactant, particularly in hydrotreating processes, to achieve oxygen removal. The present invention, however, is not so limited. Rather, as pointed out above, deoxygenation according to the present process is catalytically achieved, and amount of $H_2$ used is generally a function of the lipidic biomass feedstock. For example, when using highly saturated materials, $H_2$ can be relegated to a basically non-reactive status, being used mainly as a purge material, such as described above in relation to gas-phase catalytic deoxygenation. When using a less saturated (i.e., more olefinic) feedstock, additional $H_2$ can be used to encourage production of n-alkanes.

While Pd/C is preferred as an efficient FFA decarboxylation catalyst, the use of other catalysts is not excluded in the invention. Rather, any catalyst effective in facilitating FFA decarboxylation can be used as a catalyst in the present invention. In particular, any noble metal may be used, particularly platinum and palladium. Moreover, bimetallic catalysts may also be used according to the invention and may have the formula $M_N$-X, wherein $M_N$ is a noble metal and X is a complementary metal, which can include other noble metals or transition metals. Moreover, supports other than carbon can be used according to the invention. Non-limiting examples of supports useful according to the invention in addition to carbon include silicates, as well as any other support-type material which, preferably, is non-acidic and substantially or completely inert (i.e., have little or no inherent catalytic function). Non-limiting examples of further catalysts that could be used according to the invention include Ni, Ni/Mo, Ru, Pd, Pt, Ir, Os, and Rh metal catalysts.

The present invention is particularly distinguishable from known methods that rely on thermal decarboxylation, which require temperatures in excess of 400° C. to achieve appreciable decarboxylation. Even greater temperatures (e.g., in excess of 500° C.) can be required to achieve useful levels of decarboxylation. The present invention, however, benefits from the catalytic nature of the deoxygenation. Particularly, it is possible to proceed with significantly lower reaction temperatures while still achieving excellent deoxygenation (such as shown above in reference to FIG. 5). In certain embodiments, to carry out catalytic deoxygenation in a liquid phase reaction, the FFAs from the step one hydrolysis are heated to a temperature of up to about 325° C. In other embodiments, the FFAs are heated, in the presence of a suitable catalyst, to a temperature in the range of about 200° C. to about 320° C., about 250° C. to about 320° C., about 270° C. to about 320° C., or about 290° C. to about 310° C. Reaction pressure can be in the range of about 400 kPa to about 800 kPa, preferably about 500 kPa to about 700 kPa.

As particularly illustrated in relation to FIG. 5, catalytic decarboxylation occurs at 300° C. in the liquid-phase under conditions where there is no thermal reaction in the absence of a catalyst. Moreover, reaction selectivity for n-alkanes is very high in the catalytic process of the present invention. For example, in certain embodiments, catalytic deoxygenation occurs in a manner such that greater than 90% of the hydrocarbon reaction products are n-alkanes. In further embodiments, deoxygenation occurs in a manner such that greater than 92%, greater than 95%, greater than 97%, or greater than 98% of the hydrocarbon reaction products are n-alkanes. Such selectivity is not seen in thermal decarboxylation reactions.

In certain embodiments, catalytic deoxygenation can be described as being carried out at a temperature at which deoxygenation does not substantially proceed by thermal action alone. In other words, the catalytic reaction conditions are such that, in the absence of the catalyst, the process would result in less than 50% by weight conversion of the FFAs to their n-alkane reaction product.

The largest single energy cost in the process of the invention is the cost of heating the solvent to reaction temperature. Accordingly, in preferred embodiments, the inventive process can be optimized to minimize or eliminate the use of an added solvent in the reaction process. In one particular embodiment, the reaction can proceed in liquid n-alkane (without additional solvent) that is recycled from the reaction process. In such an embodiment, the catalyst can be used in a slurry/dispersion with the FFAs. Moreover, since the decarboxylation is proceeding catalytically and is not dependent upon temperature alone, less heat is required to maintain the lower process heat used in the catalytic decarboxylation process.

The benefits of catalytic decarboxylation according to the present invention are particularly seen in the liquid phase reaction using recycled n-alkane as the reaction solvent. As pointed out above, traditional thermal decarboxylation is typically carried out in the liquid phase using a hydrocarbon solvent, such as dodecane. Such a reaction scheme would not typically be generally regarded as being combined with a catalytic deoxygenation process. For example, is a skilled person simply sought to introduce a catalyst into a thermal decarboxylation set-up, the overall process would be hindered by the added requirement to separate the n-alkane product from the solvent, as well as the catalyst. In the present invention, however, these difficulties are overcome. For example, in certain embodiments, it is possible to use a catalyst slurry/dispersion with a solvent that is recycled n-alkane decarboxylation reaction product.

In further embodiments, the reaction can be carried out in a continuous stirred autoclave with recycling of reaction components. Further, gas phase fixed bed reactors, as well as liquid phase slurry reactors could be use. Of course, these are merely representative types of reactors and are not intended to limit the scope of the invention. One example of a method for heterogeneous catalytic deoxygenation is disclosed by Snare et al., *I. & E. Chem. Res.* 45(16) 5708-5715 (2006), which is incorporated herein by reference in its entirety.

Reforming of Long Chain Alkanes

After formation of the n-alkanes, as described above, the resulting compounds can be reformed into compounds typical of the type of fuel being prepared. For example, gasoline is generally a mixture of $C_5$-$C_{12}$ compounds, and kerosene is typically a mixture of $C_{12}$-$C_{15}$ compounds. Jet fuels, which are kerosene-based, can be prepared through reforming of n-alkanes to provide a mixture of compounds having predefined carbon chain lengths, chain conformations, and compound ratios (e.g., the mixture described in Table 1). Similarly, diesel and gasoline are both mixtures of hydrocarbon compounds in the desired chain length, chain conformation, and compound ratios. Knowing these desired compositions, it is possible to set up the reforming reaction(s) to form the compounds having the necessary chain lengths, the necessary conformations, and the necessary compound ratios to be considered the desired fuel type (i.e., either a jet engine fuel, a diesel engine fuel, or a gasoline engine fuel).

For example, as previously noted, jet fuels typically comprise n-alkanes, iso-alkanes, cyclics, and aromatics in specific ratios. Gasoline engine fuels similarly comprise varying ratios of aromatics, n-alkanes, iso-alkanes, cyclics, and alkenes. Diesel engine fuels typically have a less complex structure exhibiting a higher average molecular weight and a lower aromatic content. Standards for fuel compositions are well known, and it is particularly possible according to the present invention to prepare a particular fuel to meet a specific target composition, which can be based upon known fuel composition standards.

Reforming according to the invention can generally encompass one or more reactions that alter n-alkanes through changing the carbon chain length of the n-alkanes, changing the structure of the n-alkanes (e.g., converting from a straight chain to a branched chain or a ring structure), or altering the intramolecular bonding of the n-alkanes (e.g., converting single bonds to double bonds). For example, hydrocracking can be used to alter the chain length of alkanes, and hydroisomerization can be used to change the structure of the alkanes, such as to form a specified content of cycloalkanes and isoalkanes in the prepared fuel. Similarly, aromatization can be used to alter the intramolecular bonding of the alkanes to produce a specified content of aromatic compounds in the prepared fuel. In certain embodiments, reforming comprises two or more separate catalytic processes, each performed using different reaction parameters (such as catalyst type, temperature, pressure, or reactants). The output of the separate reforming steps can then be blended together to achieve the requisite blend of compounds to form the desired fuel composition.

For example, in one embodiment, the n-alkane stream from the deoxygenation step described above is split upon entering the reforming stage. Part of the stream may be directed to two or more separate reactors set up to carry out one or more of hydroisomerization, hydrocracking, aromatization, and cyclization. In such an embodiment, each reactor would set up under the required reaction parameters (e.g., catalysts, reactor temperature, and reactor pressure) needed to carry out the desired reaction. Each reforming reactor would reform the n-alkane stream into the desired compound(s), and the reaction product could be withdrawn from the reactor. The reaction streams from each reforming reactor could be then combined so that a final fuel product is formed having the necessary compounds in the necessary ratios to be considered a specific fuel type (e.g., jet engine fuel, diesel engine fuel, or gasoline engine fuel).

For example, in one embodiment (such as in the preparation of a jet fuel of a gasoline engine fuel), approximately 10-15% of the n-alkane stream could be diverted into a high temperature reactor set-up for forming aromatics, and the remaining portion of the n-alkane stream could be directed into an HI/HC reactor to form the necessary compounds of the required chain length (e.g., in the $C_5$-$C_{12}$ range for gasoline) and the correct conformation (e.g., cycloalkanes and olefinics). The HI/HC reaction parameters, as discussed herein, could be varied based on the desired fuel composition to provide the correct ratio of alkanes, cycloalkanes, and alkenes.

In other embodiments, though, it is possible to prepare the final fuel composition using only a single reforming reactor. For example, in fuels, such a diesel engine fuel, where aromatics are not necessarily required, all necessary reforming could be carried out in a single HI/HC reactor using suitable reaction parameters, as described herein.

In still further embodiments, it is useful to use two or more reforming reactors in series to achieve the desired final fuel composition. For example, in one embodiment, the n-alkanes from the deoxygenation step can proceed to a catalytic reactor for carrying HI/HC reactions. At least a portion of the HI/HC products can then proceed directly into a second catalytic reactor to produce aromatic and cycloalkanes. Such a reactor series set-up can be particularly useful in processes according to the invention for preparing a biogasoline product.

As illustrated by the foregoing, the present invention is particularly characterized by its broad applicability for preparing a number of fuel products. Thus, the present invention is especially beneficial because of its customizability, which arises from the recognition of a series of processes that, when carried out in series, allow the user to identify a desired fuel product and then adjust the reaction parameters as necessary to achieve production of that desired fuel. For example, as described herein the process reaction parameters can be adjusted to favor reforming of n-alkanes into hydrocarbon compounds typical of a desired fuel. The ease of forming compounds in carbon chain length, chain conformations, and compound ratios necessary to equate to a specific fuel type can, in part, depend upon the chain length of the n-alkanes entering the reforming process. Thus, to prepare a specific fuel type, it may be desirable for the n-alkanes entering the reforming process to be predominantly of a specific chain length (e.g., predominately $C_{15}$-$C_{17}$ n-alkanes). According to the present invention, it is possible to customize the deoxygenation step so that the n-alkanes produced thereby are predominately in the desired chain length range. This customization of the deoxygenation step can be facilitated by carrying out deoxygenation on FFAs that already have hydrocarbon chains in the desired length (e.g., use of a $C_{18}$ FFA, such as stearic acid, to prepare a $C_{17}$ n-alkane, such as heptadecane). The desired FFAs can be provided by beginning the process with a lipidic biomass that is rich in the desired FFAs (e.g., triglycerides having fatty acid tails of the appropriate chain length). Thus, it is clear that the entire process of the present invention can be customized to prepare a specific fuel. For example, if biogasoline is desired, the lipidic biomass can be chosen to be a material rich in triglycerides that will undergo hydrolysis to produce FFAs that will undergo deoxygenation to produce n-alkanes that can be reformed into a combination of compounds of the correct carbon chain length, chain conformation, and compound ratio necessary to meet the standards to be considered a gasoline engine fuel. The same considerations can be made to prepare a fuel that meets the requisite standards for a jet engine fuel or a diesel engine fuel.

In certain embodiments, the process of the invention can be described as including a step of recovering hydrocarbon compounds. Said step of recovering is intended to encompass any of the various methods described herein for achieving the correct combination of compounds to make up the desired fuel product. For example, in one embodiment, reforming can comprise using separate reactors to form isoalkanes, aromatics, and cycloalkanes, and the recovering step can comprise obtaining the isoalkanes, aromatics, and cycloalkanes from each, separate reactor, optionally including n-alkanes, and combining all reforming product streams in the correct n-alkanes:isoalkanes:aromatics:cycloalkanes ratio to be the desired fuel. In other embodiments, however, such as when reforming is carried out using reactors in a series or where reforming comprises the use of a single reactor, the recovering step can simply comprise collecting a single stream of hydrocarbon compounds that is already in the correct n-alkanes:isoalkanes:aromatics:cycloalkanes ratio to be the desired fuel. Thus, in separate embodiments, recovering can require a specific step of mixing individual product streams or can simply require recovering a stream that is already in the end-product form.

In various embodiments of the invention, reforming includes the use of catalysts that are chosen based on the desired end product. For hydrotreating, supported Pt is preferred, and Pt—X bimetallics (X=Ir, Re, Sn) supported on an acidic (Cl-modified) alumina are preferred for dehydrocyclization (aromatization). The desired extent of HI/HC of the n-alkane mixture from the deoxygenation step of the invention process can depend on the biofuel target (biodiesel, biogasoline, or bio jet fuel). For a biodiesel, a small degree of HI (i.e., formation of branched compounds) can be desirable for improving the cold-flow properties of the fuel. Extensive branching, though is undesirable since this will reduce the Cetane Index. For a bio-jet fuel, moderate HI/HC of the normal $C_{15}$-$C_{17}$ alkane feed can be useful to reduce the average carbon number and improve the cold-flow properties of the fuel. For a biogasoline, extensive hydrocracking of multi-branched alkanes can be useful to obtain the desired $C_4$-$C_8$ branched alkanes with high octane numbers. Over-cracking, though, to light (<$C_4$) alkanes is preferably avoided.

A delicate balance between metal and acid functions determines the performance of hydrotreating catalysts. In the present invention, catalysts prepared from amorphous oxides (e.g., silica-alumina), crystalline aluminosilicates (e.g., zeolites), and silicoalumino-phosphates (e.g., SAPO 11) with a range of Pt metal loadings can be used.

Hydroisomerization/hydrocracking (HI/HC) of the n-alkanes generally comprises contacting the n-alkanes prepared in the reduction step with a catalyst under conditions appropriate to form the desired compounds in the desired ratios, and the reforming process can particularly be carried out using a monofunctional or bifunctional solid catalyst. Reforming is particularly useful in that the process can be directed toward preparation of specific compounds depending upon the desired end product fuel. In particular, the process can be tuned to provide the desired mix of isoalkanes, cycloalkanes, and aromatics typically present in a specific fuel type. Generally, this can be achieved through controlling the following process parameters: catalyst composition structure, reaction temperature, reaction pressure, reactor residence time, and ratio of hydrogen to n-alkanes. For example, higher temperatures and decreased hydrogen pressure both favor aromatization. Parameter control and the effects thereof are more fully detailed below. Generally hydrocracking is favored using more acidic catalysts and longer residence times. Typical reaction conditions can comprise a temperature of about 350° C. to about 380° C. and a pressure of about 1 MPa to about 10 MPa.

The reforming step of the reaction can be used to prepare compounds of a variety of chain lengths, generally depending upon the desired end product and the content of the starting material (the lipidic biomass). As previously noted, animal fats generally comprise a majority of $C_{16}$ and $C_{18}$ fatty acids. Thus, a majority of the n-alkanes resulting from the reduction step described above have similar carbon chain lengths. Of course, the content of the lipidic biomass can be customized to result in the production of n-alkanes that are particularly amenable to reforming into fuels having specific compositions. Generally, the n-alkanes mixture introduced into the reforming step of the invention can comprise $C_6$-$C_{20}$ hydrocarbons. In specific embodiments, the n-alkanes mixture introduced into the reforming step of the invention can comprise $C_{15}$-$C_{17}$ hydrocarbons.

In one embodiment, the reforming is particularly customized for formation of jet fuel. In such an embodiment, the reforming can be customized to prepare a jet fuel mixture comprising primarily of $C_9$-$C_{18}$ hydrocarbons. Preferably, the mixture comprises $C_{10}$-$C_{14}$ hydrocarbons, and particularly $C_{10}$-$C_{14}$ isoalkanes. In further embodiments, the reforming step can be customized to favor formation of carbon chain lengths such that specified compound ratios can be achieved. Catalyst composition and reactor conditions can be adjusted to favor hydrocracking products (lower molecular weight compounds) or hydroisomerization products (more highly branched isomers), particularly $C_{10}$-$C_{14}$ isoalkanes.

In another embodiment, the reforming is particularly customized for formation of gasoline. In such an embodiment, the reforming can be customized to prepare a mixture of compounds comprising primarily $C_7$-$C_{11}$ hydrocarbons. Preferably, the mixture is optimized to comprise a majority of $C_8$ hydrocarbons, and particularly $C_8$ isoalkanes.

A variety of catalysts can be used according to the present invention including monofunctional and bifunctional catalysts. Monofunctional catalysts preferentially comprise a noble metal and can include bimetallics having the formula $M_N$-X, wherein $M_N$ is a noble metal and X is a complementary metal, including other noble metals. In preferred embodiments, the catalyst comprises platinum. Bifunctional catalyst comprise a metal functional component and a non-metal functional component. The metal functional component of a bifunctional catalyst according to the present invention can comprise a noble metal (or bimetallic) as described above in relation to monofunctional catalysts. The non-metal functional component of a bifunctional catalyst according to the invention preferably comprises a solid acidic material, such as an acidic metal oxide. In certain embodiments, the acid functional portion of the bifunctional catalyst can be selected from amorphous oxides (e.g., silica-alumina), aluminosilicate zeolites (e.g., γ and β), and silicoalumino-phosphates (e.g., SAPO 11). Of course, the foregoing materials are only provided as examples and are not intended to limit the scope of the invention. Rather, other solid materials providing acidic reaction sites and being capable of performing catalytic functions as described herein could be used according to the invention.

In addition to the chemical makeup, catalysts according to the invention can also vary based on physical structure. For example, a bifunctional catalyst according to the invention can be provided as discrete metal functional particles and separate discrete acidic functional particles. In a preferred embodiment, the acidic functional component forms a substrate for the metal functional component (e.g., Pt supported on silica/alumina). Moreover, a monofunctional catalyst according to the invention can comprise discrete particles of a metal functional component alone or supported on a non-functional substrate.

Reforming reactions are typically carried out at increased temperature and pressure. In certain embodiments, HI/HC reforming of n-alkanes can be carried out at a temperature of up to about 600° C., up to about 550° C., or up to about 525° C. In specific embodiments, reforming reactions are performed in a temperature range of about 300° C. to about 600° C., about 325° C. to about 550° C., about 350° C. to about 500° C., about 350° C. to about 450° C., or about 400° C. to about 450° C. Reactor vessel pressure during reforming is typically in the range of about 0.5 MPa to about 20 MPa, about 1 MPa to about 15 MPa, or about 1 MPa to about 10 MPa. Preferably, the reactions are carried out in a hydrogen atmosphere. In reactions such as dehydrocyclization, optimum hydrogen pressure can be varied as necessary to suppress coke accumulation (mainly from polycyclic aromatic hydrocarbons) leading to catalyst deactivation.

The selectivity of hydroisomerization/hydrocracking can be controlled according to the invention through controlling the balance between the metal and acid functions of the bifunctional HI/HC catalyst. In particular, the content of the metal functional portion of the bifunctional catalyst can vary over a range of metal loadings. For example, in a bifunctional catalyst, the metal functional component can comprise up to about 50% by weight of the catalyst, up to about 40%, up to about 30%, up to about 20%, up to about 10%, or up to about 5% by weight of the catalyst. In specific embodiments, the metal functional component comprises about 0.01% to about 10% by weight of the catalyst, about 0.02% to about 9% by weight, about 0.05% to about 8% by weight, about 0.1% to about 7% by weight, about 0.1% to about 6% by weight, or about 0.1% to about 5% by weight of the catalyst.

The reforming effect can also be controlled by altering the reaction temperature and pressure within the previously described ranges. For example, higher reaction temperatures (in the range of 400-450° C.) and lower hydrogen pressures will generally favor dehydrocyclization of alkanes to form aromatics. Further, higher temperatures and higher conversions will generally favor hydrocracking over hydroisomerization.

Petroleum-derived fuels (especially jet fuel and gasoline) contain cycloalkanes and aromatic compounds. Consequently, to ensure complete compatibility of second generation biofuels with existing engines, it may be necessary to produce cycloalkanes and aromatics from bio-renewable fats and oils. Accordingly, reforming reaction parameters can further be controlled to favor vapor-phase dehydrocyclization (DHC) of alkanes to aromatics. Aromatization and cyclization of n-alkanes can be achieved, according to certain embodiments of the invention, using supported metal catalysts (preferably Pt-containing catalysts). High temperatures (such as about 400-450° C.) are useful for dehydrocyclization (DHC) of alkanes to aromatics, since the reaction is strongly endothermic. The DHC mechanism can involve only the transition metal (monofunctional catalytic pathway) or the transition metal and acid sites of the support (bifunctional catalytic pathway) depending on the catalyst composition. For example, Pt supported on a non-acidic K-exchanged L zeolite (a monofunctional pathway) is selective for benzene formation from n-hexane via monofunctional catalysis (1-6 ring closure). Methylcyclopentane resulting from 1-5 ring closure also occurs over Pt, and the ratio of 1-6 to 1-5 ring closure products from n-hexane can be controlled by controlling the pore geometry for non-acidic supports.

In further embodiments, alkane DHC can be carried out via a bifunctional pathway through use of conventional reforming catalysts, such as Pt or a PtX bimetallic (particularly wherein X=Ir, Re, Sn) supported on an acidic alumina support (such as Cl-modified supports). For example, conventional petroleum naphtha reforming catalysts that are used to produce high-octane unleaded gasoline catalyze alkane dehydrocyclization via a bifunctional pathway. As previously described, the metal catalytic sites (e.g., noble metals) provide a dehydrogenation/hydrogenation function, and adsorption of the resulting olefins on acid sites of the support generates alkyl carbenium ions. The more stable secondary carbenium ion undergoes 1-5 ring closure to yield methylcyclopentane. Subsequent metal- and acid-catalyzed reactions lead to cyclohexane and ultimately benzene. This is particularly useful according to the invention in that it allows for the reforming of a $C_{15}$-$C_{17}$ alkane feedstock to a surrogate JP-8 fuel. Specifically, dehydrocyclization of higher alkanes, such as the $C_8$-$C_9$ compounds in petroleum naptha, over bifunctional catalysts results directly in 1-6 ring closure products, such as alkyl-substituted benzenes. Tests using n-tridecane and n-hexadecane as model compounds illustrated that aromatics (such as toluene, xylenes, and methyl- and dimethylnapthalenes) can be prepared in addition to hydroisomerization products. The optimum hydrogen pressure for dehydrocyclization is determined by the need to suppress coke (mainly polycyclic aromatic hydrocarbons) accumulation leading to catalyst deactivation.

In one embodiment, hydroisomerization/hydrocracking of the n-alkanes produced in the previous catalytic deoxygenation step can be achieved using a bifunctional solid catalyst consisting of platinum supported on an acidic metal oxide. The Pt sites provide a dehydrogenation/hydrogenation function, and adsorption of the resulting alkenes (olefins) on the acid sites generates secondary carbenium ions. These carbenium ion intermediates undergo skeletal isomerization to more stable tertiary carbenium ions before donating a proton (H+) to regenerate the acid site. Subsequent hydrogenation of the resulting alkene (at a Pt site) produces mono-, di-, and tri-branched alkanes. Hydrocracking is a closely related process resulting from β-scission of the carbenium ion intermediate. The extent of the hydrocracking can be controlled to impart particular properties to the resulting fuel product. For example, a limited amount of cracking of the alkane feed can be carried out to reduce the average carbon number as necessary to improve the cold-flow properties of the fuel. A schematic of a typical isomerization/hydrocracking network is shown in FIG. 11.

With the appropriate balance of Pt and acid sites, the primary reaction products are mono-branched alkanes. Multi-branches alkanes are secondary products and hydrocracking products (a mixture of medium and low molecular weight species, relative to the original n-alkanes) are formed in series from the multi-branched species. Consequently, higher n-alkane conversion will favor hydrocracking products.

In a specific embodiment, a catalyst useful in a reforming step of the inventive process comprises a 1% by weight Pt on zeolite Y (Pt/Y) prepared by ion exchange. Such a catalyst was used, in one embodiment, for the reaction of liquid n-heptadecane at 300° C. in a 50 mL stirred autoclave reactor under 500 psig $H_2$. The reaction products after three hours reaction time are illustrated in the chromatogram shown in FIG. 12. As seen therein, the major products are $C_{17}$ branched alkanes (including methyl, dimethyl, and trimethyl branched isomers). Also observed are $C_5$-$C_{14}$ hydrocracking products. Due to the underlying carbenium ion (β-scission) mechanism, the yields of $C_{16}$ and $C_{15}$ species from the $C_{17}$ feedstock are negligible. GC and quadrupole mass spectrometry of the gas-phase products revealed small quantities of methane, ethane, propane, and butane. Evaluations using a 1 wt % Pt on mordenite (Pt/M) catalyst demonstrated higher yields of hydrocracking products under similar reactions.

In certain embodiments, it is possible according to the invention to provide catalysts and conditions that are particularly useful for producing biogasoline, particularly from a deoxygenation reaction stream comprising $C_{17}$ n-alkanes. In one embodiment, an evaluation was carried out using liquid n-heptadecane and a Pt catalyst in a 100 mL batch reactor at 300° C. and 1000 psig $H_2$. The heptadecane conversion after 30 minutes was essentially 100%, and greater than 95% by mass was converted to liquid products. Gas chromatograph-mass spectrometer (GC-MS) analysis, as shown in FIG. 13, indicated that the products were a mixture of branched and linear alkanes. No aromatics or cycloalkanes were detected. Gas-phase products consisted primarily of $C_1$-$C_4$ hydrocarbons.

The carbon number distribution obtained after one hour batch hydrotreating using the same catalyst and conditions was similar to that of a typical regular unleaded gasoline, especially given the absence of cycloalkanes and aromatic compounds ($C_6$ and above). This is illustrated in FIG. 14. This figure also illustrates the progressive nature hydrocracking A 30 minute batch time yields a higher average molecular weight and more product in the middle distillate (kerosene or jet fuel) range compared to a one hour batch time.

Energy Recovery

The process of the invention is further characterized by the multiple available options for optimizing efficiency by converting as much as possible of the energy content of the lipidic biomass into useable fuel. This is achieved by methods including, but not limited to, recovery and re-use of excess steam from the hydrolysis process, combustion of glycerol by-product of the hydrolysis process with heat exchange to all three chemical process, and recovery of internal energy of exiting fuel product by heat exchange to all three chemical processes.

A useful figure of merit related to energy balance is the energy conversion efficiency, as defined below in Formula (11), where LHV is the lower heating value.

$$\text{Energy Efficiency} = \frac{LHV \text{ of Produced Fuel}}{(LHV \text{ of Reactants} + \text{Input Energy})} \quad (11)$$

Determining conversion efficiency must take into account multiple factors. Table 5 below provides examples of material properties that can be used according to one embodiment of the invention for preparing jet fuel to calculate energy efficiency of the inventive process. Of course, similar considerations would come into play in other embodiments of the inventive process, such as in the preparation of biogasoline or biodiesel.

TABLE 5

| Material | Energy Content (kJ/kg) | Specific Heat (kJ/Kg · K) | Density (kg/m$^3$) |
|---|---|---|---|
| Triglyceride | 39,000 | 2.21 | 925 |
| Free Fatty Acid | 39,000 | 2.00 | 847 |
| Water | 0 | 4.20 | 1,000 |
| Glycerol | 16,700 | 2.38 | 1,261 |
| Hydrogen | 120,911 | 14.50 | 0.089 |
| n-alkanes | 47,279 | 1.90 | 111 |
| JP-8 | 44,000 | 2.00 | 820 |

A detailed process flow according to one embodiment of the invention showing each process step is provided in FIG. 15. Table 6 below summarizes the energy input and output of the process (without implementation of the energy conservation methods outlined below) for the production of 100 liters of bio-JP8 prepared according to this embodiment of the invention.

TABLE 6

| Process No. | Description | Composition | Energy Added |
|---|---|---|---|
| 1 | | Water | |
| 2 | Pump power | Water | 0.08 kW |
| 3 | Heat exchanger | Water | |
| 4 | Heater power | Water | 0.17 kW |
| 5 | Inlet energy feedstock | Triglycerides | 54.93 kW |
| 6 | Pump power | Triglycerides | 0.13 kW |
| 7 | Heat Exchanger | Triglycerides | |
| 8 | Heater power | Triglycerides | 0.28 kW |
| 9 | Step 1 reactor/line make-up heat | Water/Glycerine | 0.70 kW |
| 10 | | Free Fatty Acids | |
| 11 | Glycerine by-product | Water/Glycerine | |
| 12 | | Free Fatty Acids | |
| 13 | Step 1 product stored @ ambient | Free Fatty Acids | |
| 14 | Pump power | Free Fatty Acids | 0.12 kW |
| 15 | Heat exchanger | Free Fatty Acids | |
| 16 | Heater power | Free Fatty Acids | 0.29 kW |
| 17 | Step 2 reactor/line make-up heat | n-alkanes | 1.10 kW |
| 18 | Inlet energy in $H_2$ | He/$H_2$ | 1.68 kW |
| 19 | Adiabatic compression power | He/$H_2$ | 0.05 kW |
| 20 | He/$H_2$ not recycled | He $H_2$, $CO_2$ | |
| 21 | | n-alkanes | |
| 22 | Step 2 product stored @ ambient | n-alkanes | |
| 23 | Pump power | n-alkanes | 0.10 kW |
| 24 | Heat exchanger | n-alkanes | |
| 25 | Heater power | n-alkanes | 0.25 kW |
| 26 | Step 3 reactor/line heat leak | JP-8 | 1.70 kW |
| 27 | Inlet energy in $H_2$ | He/$H_2$ | 1.68 kW |
| 28 | Adiabatic compression power | He/$H_2$ | 0.05 kW |
| 29 | He/$H_2$ not recycled | He/$H_2$ | |
| 30 | Light hydrocarbons not used | Light hydrocarbons | |
| 31 | 45.1 kW contained in 100 L JP8 | JP-8 | |

The total energy added to the system shown in Table 6 (63.31 kW) is the denominator in Formula (10) above. The numerator is only that energy that is contained in the 100 liters of bio-JP8 fuel produced (45.1 kW). Calculation according to Formula (10) shows an energy efficiency of 71.2% without inclusion of any energy conservation steps, as described below. Thus, this represents a conservative energy efficiency since all energy calculations are based on actual hardware power consumption curves (pumps and compressors), heat transfer effectiveness values (heat exchangers=0.7), insulation R-values (line heaters and heat loss in the reactors), and reactor throughput material loss (glycerol in Step 1, $CO_2$ in Step 2, and light hydrocarbons in Step 3.

In particular embodiments, the process of the invention requires a total thermal input of approximately 2.3 MJ/kg of animal fat used as the lipidic biomass fuelstock. To minimize this heat input, the process is generally designed to maximize the heat recovery from the end products in preheating the fat and water in the first stage. The hydrolysis step can particularly be optimized according to the invention to recover energy for use in the process. For example, the hot glycerol/water mixture prepared by fat hydrolysis can be separated by flash evaporation of water, to yield glycerol with sufficient purity to burn efficiently in a combustor, and the hot water can be recycled to the hydrolysis process. Taking into account the energy losses due to non-ideal processes, such approaches can restore up to about two-thirds of the thermal input energy required.

Thus, in certain embodiments, the process of the present invention comprises recovering at least a portion of the glycerol prepared in the hydrolysis step and recycling the glycerol as an energy source. The energy content of the glycerol produced in the hydrolysis step is actually sufficient to provide the necessary reactor heating for all three steps of the inventive process, as well as provide heat to reactors to alleviate heat loss to the environment during operation. Realization of the heating energy available in the glycerol by-product can particularly be via a proprietary method and apparatus provided by the inventors of the present invention.

Glycerol combustion can, in one embodiment, proceed via a proprietary method and apparatus provided by the inventors of the present invention. For example, the glycerol combustion can be carried out in an insulated burner with a glycerol combustion chamber. Preferably, the glycerol combustion chamber is pre-heated, and the glycerol recovered from the hydrolysis step of the present invention is introduced directly into the pre-heated glycerol combustion chamber. Optionally, the glycerol can be treated to reduce the glycerol viscosity. The glycerol can be atomized prior to introduction into the glycerol combustion chamber. Upon introduction of the glycerol into the combustion changer, the atomized glycerol is combined with air and combusted to produce heat.

Pre-heating of the glycerol combustion chamber can be carried out according to various methods, such as combustion of a start-up fuel source or use of resistance heating. In one embodiment, the pre-heating step comprises combustion of a non-glycerol fuel source (i.e., a start-up fuel source) within the glycerol combustion chamber. This is preferably carried out for a period of time sufficient to heat the combustion chamber to a temperature at least equal to the auto ignition temperature of glycerol. After the desired temperature has been achieved, introduction of the non-glycerol fuel source can be discontinued and fully replaced with glycerol. The transition between the start-up fuel source and the glycerol can be gradual or distinct.

In specific embodiments, the step of treating the glycerol to reduce the viscosity thereof comprises reducing the viscosity of the glycerol to less than a specified viscosity. Preferably, the glycerol viscosity is reduced to less than about 20 centistokes. In specific embodiments, the step of treating the glycerol comprises heating the glycerol source, such as up to a temperature of at least 91° C. In another embodiment the treating step comprises combining the glycerol with a viscosity-reducing liquid, which preferentially also is combustible (e.g., kerosene).

In yet another embodiment the step of combining the atomized glycerol with air comprises providing an aerodynamically restricted air flow such that the atomized glycerol is introduced into the glycerol combustion chamber with a defined flow pattern and air mixture. In a specific embodiment, such aerodynamically restricted air flow is provided by a swirl component.

Glycerol combustion for providing heat in the present inventive process can particularly be carried out using a specifically designed glycerol combustion apparatus. In one embodiment, the apparatus comprises the following: an insulated glycerol combustion chamber being formed to provide radiant and convective feedback heating; a glycerol input line for introduction of the glycerol into the glycerol combustion chamber, wherein the line includes one or more components for heating or maintaining the glycerol within the line at a temperature of at least about 91° C.; an atomizer attached to the glycerol input line capable of atomizing the glycerol prior to introduction of the glycerol into the glycerol combustion chamber; and an air flow component for combining air with the atomized glycerol source, wherein the air flow component includes aerodynamic restrictions useful to provide a desired flow pattern when combined with the atomized glycerol.

A glycerol burner, such as the one described above, can be integrated into the process reactor set-up in the present invention and used to produce process steam (e.g., approximately 400° C.), which can then be plumbed to dedicated heat exchangers in the stream flows and to jacketed reactors to mitigate heat loss to the surroundings.

Combustion of glycerol generally proceeds according to Formula (12),

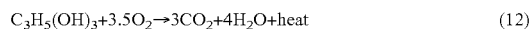

$$C_3H_5(OH)_3 + 3.5O_2 \rightarrow 3CO_2 + 4H_2O + \text{heat} \qquad (12)$$

and the heat of combustion is approximately 16 MJ/kg of glycerol. Thus, it is clear that combustion of glycerol requires provision of the glycerol itself, as well as a combustion-sustaining amount of oxygen (often supplied from ambient air). The prior art, however, has heretofore failed to recognize the combination of variables that must be established and combined to achieve the clean and efficient combustion of glycerol and thus provide the ability to both directly withdraw glycerol as a side-stream of an industrial process and use the glycerol by-product as a fuel source for generating heat.

Generally, a standard fuel oil burner cannot easily combust glycerol due to the high viscosity of the material. Likewise, the relatively high auto ignition temperature of glycerol also reduces the ability to combust in a standard oil burner. Previous attempts at burning glycerol have illustrated the associated difficulties. For example, many burners do not burn at a sufficiently high temperature to maintain combustion, which results in formation of sticky residues that can clog the burner and self-extinguish the combustion. Attempts to combust glycerol using a standard fuel burning apparatus, such as a kerosene heater, have proven unsuccessful, even when trying to burn the glycerol using a continuous spark ignition source. In fact, glycerol does not evenly and efficiently combust even in the presence of a sustained flame. This is illustrated by placing a propane torch into a glycerol spray. The glycerol in the immediate vicinity of the propane-fed flame will burn, but there is incomplete combustion of the entire glycerol spray, and glycerol burn is not self-sustaining after removal of the propane-fed torch. Such a method of burning glycerol is also potentially hazardous because of the presence of localized variations in the glycerol flowfield where the glycerol is above its thermal decomposition temperature but below its auto-ignition temperature. Such an environment can result in the formation of undesirable species, such as acrolein.

Glycerol combustion, however, is made possible according to the method and apparatus that is more fully described in Applicant's co-pending U.S. Provisional Patent Application No. 60/942,290, the disclosure of which is incorporated herein by reference. As such, glycerol combustion in the process of the present invention is possible by provision of an apparatus comprising a suitable glycerol combustion chamber, introduction of the glycerol into the combustion chamber in a state designed to maximize combustibility of the glycerol, and provision of air via a route also designed to maximize combustibility of the glycerol.

The present invention also encompasses further processes that can be useful for increasing conversion efficiency up to 90%, or even greater. Exemplary processes include catalyst optimization, enzymatic processes, plasma processing, and reforming of glycerol to higher-value products (e.g., propylene glycols).

In certain embodiments, the process of the present invention is carried out as a continuous flow process. In other words, all steps in the inventive process are carried out sequentially, with the reaction product from the hydrolysis step (i.e., the free fatty acids) being moved directly into the catalytic deoxygenation step, and the reaction product from the catalytic deoxygenation step (i.e., the n-alkanes) being moved directly into the reforming step. Such a continuous flow process provides for improved energy efficiency since a single system pressurization function can be performed. If the process steps are performed in three separate batch processes, however, three separate pressure cycles must be performed, which increases the energy input.

Hydrogen generated in the reforming step of the inventive process can be used in the catalytic deoxygenation step of the inventive process, as described above. Recirculating the hydrogen product instead of disposing the hydrogen thus further increases the energy efficiency of the process.

Still further, as described previously, improved catalyst performance can also increase energy efficiency. For example, the reforming step of the process can result in formation of a certain content of light hydrocarbons (LHC, e.g., $C_1$-$C_5$). Such LHC are typically not desired for transportation fuels, such as jet fuel, diesel, and gasoline. Use of preferred catalysts, such as described herein, can reduce the LHC content. Preferably, the catalyst used in the reforming step leads to a produced LHC content of less than about 20% by weight, based on the overall weight of the reaction product from the reforming process. In certain embodiments, the reforming step leads to a produced LHC content of less than about 15% by weight, less than about 12% by weight, less than about 10% by weight, less than about 8% by weight, less than about 5% by weight, less than about 4% by weight, less than about 3% by weight, less than about 2% by weight, or less than about 1% by weight, based on the overall weight of the reaction product from the reforming process.

By combining the various energy conservation steps described herein, it is possible to greatly increase the overall energy efficiency of the inventive process. For example, Table 7 below summarizes several process improvements that can be used to increase energy efficiency. Table 7 further illustrates one embodiment of the invention wherein it is possible to realize greater than 86% efficiency for the overall process of the invention.

TABLE 7

| Process Efficiency Enhancement | Energy Savings (kW) | Cumulative Efficiency Energy | Mass |
|---|---|---|---|
| Process without energy enhancements | — | 71.2% | 72.8% |
| Continuous flow deletes pumps at start of catalytic deoxygenation step and reforming step | 0.22 | 71.5% | 72.8% |
| Burn glycerol from hydrolysis step in recovery boiler and use steam to replace heaters | 0.99 | 72.6% | 72.8% |
| Burn glycerol in recovery boiler and use steam in jacketed reactors to eliminate heat loss | 3.50 | 77.0% | 72.8% |
| Reuse recovered H2/He in Reforming step so H2 energy is not wasted | 1.68 | 79.2% | 72.8% |
| Reuse recovered H2/He in catalytic deoxygenation step so H2 energy is not wasted | 1.68 | 81.6% | 72.8% |
| Implement catalyst improvements in reforming step to reduce LHC generation to 5% | 0.22 | 86.2% | 76.8% |

Table 7 begins with the actual efficiency of a non-optimized process, as described above in relation to Table 6. However, through implementation of the various energy conservation steps described herein, it is clearly possible to increase the overall efficiency of the inventive process to in excess of 86%. Accordingly, in specific embodiments, the process of the invention is useful for preparing a bio-fuel, wherein the overall process exhibits an energy efficiency of at least about 75%, at least about 80%, at least about 85%, at least about 86%, or at least about 90%, wherein energy efficiency is calculated according to Formula (10).

Biofuel Characterization

Biofuels prepared according to the present invention preferably meet a number of physical and chemical properties indicating functional equivalence to refined hydrocarbon distillate fuel oil. In particular, volatility, freezing point, and viscosity should generally be within specified limits. Combustion properties of importance include auto-ignition, energy content, and flame strength (characterized by both the extinction strain rate and premixed laminar burning velocity).

To ensure the operational safety of jet fuels, volatility must be low. In one embodiment, volatility can be measured by the flash point, the lowest temperature at which application of a test flame causes the vapor above the sample to ignite. Preferably, jet fuels prepared according to the invention exhibits a flash point of at least 38° C., as required by MIL-DTL-83133E. The flash point can particularly be measured using the Pensky-Martens closed cup tester (ASTM Standard Test Method D 93-00 Flash Point by Tag Closed Tester). In order to meet the low volatility requirement, the inventive process can be carried out to prevent generation of short alkanes (i.e., less than approximately 8 carbons) during alkane synthesis.

Due to the low temperatures associated with high altitude flight operations, the freezing point, defined as the temperature below which solid hydrocarbon crystals may form, of jet fuel prepared according to the invention should be at most −47° C. The freezing point can be measured using a simple manual technique following the ASTM D 2386 Freezing Point of Aviation Fuels test procedure.

Viscosity can be measured using a standard reference capillary viscometer following the test procedure called out by ASTM D 4451 Kinematic Viscosity of Transparent and Opaque Liquids. Preferably, jet fuel prepared according to the invention has a viscosity of no greater than 8.0 mm²/s at −20°

C. Such can particularly be achieved by increasing the content of isoalkanes in the fuel product.

The auto-ignition of a fuel is a function of both the temperature and flow field. To understand the fundamental chemical kinetics, the ignition temperature as a function of hydrodynamic strain rate is measured in a simple one-dimensional flame. In practice, the fuel is vaporized in hot nitrogen and then advected into a counterflow diffusion flame burner, flowing against a heated stream of air. The hydrodynamic strain rate scales linearly with the fuel and oxidizer flow velocities. A stream of vaporized fuel flows against a heated stream of air at a given temperature at an initially high strain rate. At this strain rate, the residence time is too short for chain branching reactions to occur and the fuel does not ignite. As the flow rates are decreased, the strain rate decreases, decreasing the scalar dissipation rate, increasing the residence time, and this continues until ignition abruptly occurs. The measurements are then repeated at a different air temperature, building an ignition curve. The ignition curve determined for a biofuel prepared according to the invention can be compared against ignition curves for various stocks of JP-8. The ignition curve is a strong function of the aromatic content and can be related to the Cetane Index.

Another important chemical kinetic parameter is the strain rate at extinction. This is similar to the ignition strain rate-temperature correlation, but a flame is ignited in a counterflow geometry at a low strain rate and the strain rate is incrementally increased until the flame globally extinguishes. This measurement is made as a function of air temperature and can be compared with results for JP-8.

A third chemical kinetic parameter of importance is laminar burning velocity, which can be measured in a combustion bomb with optical access employing a high-speed intensified camera. A fourth chemical parameter to be measured is the smoke point, a fundamental measure of the fuels propensity to soot. This is important not only from an emissions view point (ability of an adversary to track and target the aircraft) but also an indirect measure of the aromatic content of the fuel.

The energy content, in kJ/kg, can be measured in a bomb calorimeter using the ASTM D 4809 Heat of Combustion of Liquid Hydrocarbon Fuels by Bomb calorimeter method. Preferably, a jet fuel prepared according to the invention exhibits an energy content of at least about 42,800 kJ/kg.

Many modifications and other embodiments of the inventions set forth herein will come to mind to one skilled in the art to which these inventions pertain having the benefit of the teachings presented in the foregoing descriptions. Therefore, it is to be understood that the inventions are not to be limited to the specific embodiments disclosed and that modifications and other embodiments are intended to be included within the scope of the appended claims. Although specific terms are employed herein, they are used in a generic and descriptive sense only and not for purposes of limitation.

That which is claimed:

1. A process for the direct conversion of lipidic biomass to a transportation fuel, said process comprising:
   (A) performing thermal hydrolysis on a lipidic biomass to form a product stream comprising a free fatty acid and form a by-product stream comprising glycerol;
   (B) performing catalytic deoxygenation on the free fatty acid stream by one or both of a decarboxylation reaction pathway or a decarbonylation reaction pathway by heating the free fatty acid stream in the presence of a catalyst to form a product stream comprising an n-alkane; and
   (C) performing one or more reforming steps on the n-alkane stream to form a product stream comprising a mixture of hydrocarbon compounds selected from the group consisting of n-alkanes, isoalkanes, aromatics, and cycloalkanes;
   wherein, after step (C), the hydrocarbon compounds in the product stream are in a combination and ratio necessary to form an overall composition useful as the transportation fuel.

2. The process according to claim 1, wherein the lipidic biomass comprises a material selected from the group consisting of triglycerides, diglycerides, monoglycerides, free fatty acids, and combinations thereof.

3. The process according to claim 1, wherein the lipidic biomass comprises a material selected from the group consisting of animal fat, vegetable oil, algae lipids, waste grease, or mixtures thereof.

4. The process according to claim 3, wherein the lipidic biomass source comprises animal fat selected from the group consisting of beef fat, hog fat, turkey fat, and chicken fat.

5. The process according to claim 1, wherein one or more process steps requires application of heat, and wherein the process further comprises recovering at least a portion of the glycerol stream and using the glycerol as a fuel for producing at least a portion of the process heat.

6. The process according to claim 1, wherein said thermal hydrolysis step comprises introducing the lipidic biomass into the bottom of a reactor column, introducing water near the top of the reactor column, and heating the reactor to a temperature of about 220° C. to about 300° C. under a pressure sufficient to prevent the water in the reactor from flashing to steam.

7. The process according to claim 1, wherein said catalytic deoxygenation step comprises gas-phase deoxygenation.

8. The process according to claim 7, wherein said catalytic deoxygenation step comprises the use of a fixed-bed catalyst.

9. The process according to claim 8, wherein the fixed-bed catalyst comprises a noble metal.

10. The process according to claim 8, wherein the fixed-bed catalyst comprises palladium.

11. The process according to claim 1, wherein said catalytic deoxygenation step comprises liquid-phase catalytic deoxygenation carried out in a hydrocarbon solvent.

12. The process according to claim 1, wherein said catalytic deoxygenation is carried out at a temperature of up to 325° C.

13. The process according to claim 11, wherein said catalytic deoxygenation step comprises the use of a catalyst slurry or catalyst dispersion.

14. The process according to claim 13, wherein the catalyst in the catalyst slurry or catalyst dispersion comprises a noble metal.

15. The process according to claim 13, wherein the catalyst in the catalyst slurry or catalyst dispersion comprises palladium.

16. The process according to claim 11, further comprising recovering a portion of the n-alkane stream formed in said catalytic deoxygenation step and using the n-alkane stream as at least a portion of the hydrocarbon solvent in which the liquid phase catalytic deoxygenation step is carried out.

17. The process according to claim 1, wherein said catalytic deoxygenation step further comprises the addition of $H_2$.

18. The process according to claim 1, wherein said catalytic deoxygenation is carried out at a temperature at which deoxygenation does not substantially proceed by thermal action alone.

19. The process according to claim 1, wherein the one or more reforming steps are selected from the group consisting of hydroisomerization, hydrocracking, dehydrocyclization, and aromatization.

20. The process according to claim 1, wherein said reforming comprises the use of a solid catalyst.

21. The process according to claim 20 wherein the solid catalyst comprises a metal functional component.

22. The process according to claim 21, wherein the solid catalyst further comprises an acidic-functional component.

23. The process according to claim 1, wherein said reforming comprises the use of two or more different catalysts.

24. The process according to claim 1, wherein step (C) comprises a first reaction carried out in a first reactor and at least a second reaction carried out in at least a second, separate reactor.

25. The process according to claim 24, wherein step (C) further comprises separating the n-alkane stream into two or more reforming streams and directing the two or more reforming streams separately into the first reactor and the at least second reactor.

26. The process according to claim 24, wherein the first reactor and the at least second reactor are in series such that a first reforming product stream is formed in the first reactor and the first reforming product stream proceeds to the at least second reactor, wherein is formed a second reforming product stream.

27. The process according to claim 1, wherein step (C) comprises a first reaction carried out in a first reactor, a second reaction carried out in a second, separate reactor, and at least a third reaction carried out in at least a third, separate reactor.

28. The process according to claim 1, wherein the hydrocarbon compounds in the product stream are in a combination and ratio necessary to form an overall composition useful as a jet engine fuel.

29. The process according to claim 1, wherein the hydrocarbon compounds in the product stream are in a combination and ratio necessary to form an overall composition useful as a gasoline engine fuel.

30. The process according to claim 1, wherein the hydrocarbon compounds in the product stream are in a combination and ratio necessary to form an overall composition useful as a diesel engine fuel.

31. The process according to claim 1, wherein the overall composition formed is substantially identical to a petroleum-derived transportation fuel selected from the group consisting of jet engine fuel, gasoline engine fuel, and diesel engine fuel.

32. The process according to claim 1, wherein steps (A)-(C) are carried out separately and sequentially.

33. A bio-jet fuel that is substantially identical in composition to a petroleum-derived jet engine fuel, the bio jet fuel being prepared according to the process of claim 1.

34. A bio-gasoline that is substantially identical in composition to a petroleum-derived gasoline engine fuel, the bio-gasoline being prepared according to the process of claim 1.

35. A bio-diesel that is substantially identical in composition to a petroleum-derived diesel engine fuel, the bio-diesel being prepared according to the process of claim 1.

36. A process for the direct conversion of lipidic biomass to a transportation fuel, said process comprising:
 (A) performing thermal hydrolysis on a lipidic biomass to form a product stream comprising a free fatty acid and form a by-product stream comprising glycerol;
 (B) performing catalytic deoxygenation on the free fatty acid stream by one or both of a decarboxylation reaction pathway or a decarbonylation reaction pathway by heating the free fatty acid stream in the presence of a catalyst to form a product stream comprising an n-alkane;
 (C) performing one or more reforming steps on the n-alkane stream to form a product stream comprising a mixture of hydrocarbon compounds selected from the group consisting of n-alkanes, isoalkanes, aromatics, and cycloalkanes; and
 (D) using at least a portion of the glycerol stream as a fuel for producing heat, at least a portion of which is used to provide heat to one or more process steps;
 wherein, after step (C), the hydrocarbon compounds in the product stream are in a combination and ratio necessary to form an overall composition useful as the transportation fuel.

37. A process for the direct conversion of lipidic biomass to a transportation fuel, said process comprising:
 (A) performing thermal hydrolysis on a lipidic biomass by heating the lipidic biomass to a temperature of up to about 300° C. in the presence of water to form a product stream comprising a free fatty acid and form a by-product stream comprising glycerol;
 (B) performing catalytic deoxygenation on the free fatty acid stream by one or both of a decarboxylation reaction pathway or a decarbonylation reaction pathway by heating the free fatty acid stream to a temperature of up to 325° C. in the presence of a catalyst comprising a noble metal to form a product stream comprising an n-alkane; and
 (C) performing one or more reforming steps selected from the group consisting of hydroisomerization, hydrocracking, dehydrocyclization, and aromatization on the n-alkane stream to form a product stream comprising a mixture of hydrocarbon compounds selected from the group consisting of n-alkanes, isoalkanes, aromatics, and cycloalkanes;
 wherein, after step (C), the hydrocarbon compounds in the product stream are in a combination and ratio necessary to form an overall composition useful as the transportation fuel.

38. A process for the direct conversion of lipidic biomass to a transportation fuel, said process comprising:
 (A) performing thermal hydrolysis on a lipidic biomass to form a product stream comprising a free fatty acid and form a by-product stream comprising glycerol;
 (B) performing liquid-phase catalytic deoxygenation on the free fatty acid stream in a hydrocarbon solvent by one or both of a decarboxylation reaction pathway or a decarbonylation reaction pathway by heating the free fatty acid stream in the presence of the catalyst to form a product stream comprising an n-alkane; and
 (C) performing one or more reforming steps on the n-alkane stream to form a product stream comprising a mixture of hydrocarbon compounds selected from the group consisting of n-alkanes, isoalkanes, aromatics, and cycloalkanes;
 wherein, after step (C), the hydrocarbon compounds in the product stream are in a combination and ratio necessary to form an overall composition useful as the transportation fuel.

39. The process according to claim 38, further comprising recovering a portion of the n-alkane stream formed in said catalytic deoxygenation step and using the n-alkane stream as at least a portion of the hydrocarbon solvent in which the liquid-phase catalytic deoxygenation step is carried out.

40. A process for the direct conversion of lipidic biomass to a transportation fuel, said process comprising:

(A) performing thermal hydrolysis on a lipidic biomass to form a product stream comprising a free fatty acid and form a by-product stream comprising glycerol;

(B) performing catalytic deoxygenation on the free fatty acid stream by one or both of a decarboxylation reaction pathway or a decarbonylation reaction pathway using a fixed-bed catalyst by heating the free fatty acid stream in the presence of the catalyst to form a product stream comprising an n-alkane; and (C) performing one or more reforming steps on the n-alkane stream to form a product stream comprising a mixture of hydrocarbon compounds selected from the group consisting of n-alkanes, isoalkanes, aromatics, and cycloalkanes;

wherein, after step (C), the hydrocarbon compounds in the product stream are in a combination and ratio necessary to form an overall composition useful as the transportation fuel.

* * * * *